(12) United States Patent
Goldfain et al.

(10) Patent No.: US 7,311,401 B2
(45) Date of Patent: *Dec. 25, 2007

(54) EYE VIEWING DEVICE COMPRISING EYEPIECE AND VIDEO CAPTURE OPTICS

(75) Inventors: Ervin Goldfain, Syracuse, NY (US); Chris R. Roberts, Skaneateles, NY (US); Allan I. Krauter, Skaneateles, NY (US); Steven R. Slawson, Camillus, NY (US); William H. Lagerway, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 562 days.

This patent is subject to a terminal disclaimer.

(21) Appl. No.: 09/862,636

(22) Filed: May 22, 2001

(65) Prior Publication Data

US 2002/0097379 A1 Jul. 25, 2002

Related U.S. Application Data

(63) Continuation-in-part of application No. 09/783,481, filed on Feb. 14, 2001, which is a continuation-in-part of application No. 09/444,161, filed on Nov. 22, 1999, which is a continuation-in-part of application No. 09/198,545, filed on Nov. 24, 1998, now Pat. No. 6,065,837.

(60) Provisional application No. 60/206,356, filed on May 23, 2000.

(51) Int. Cl.
*A61B 3/10* (2006.01)
*A61B 3/02* (2006.01)

(52) U.S. Cl. .................. 351/221; 351/200; 351/240; 351/243

(58) Field of Classification Search .............. 351/200, 351/204–207, 209, 210, 211, 212, 215, 216, 351/218, 221, 231, 233, 240, 243, 244, 246
See application file for complete search history.

(56) References Cited

U.S. PATENT DOCUMENTS

| 3,586,424 | A | 6/1971 | Schenk |
| 3,614,214 | A | 10/1971 | Cornsweet et al. |
| 3,638,641 | A | 2/1972 | Abromavage et al. |

(Continued)

FOREIGN PATENT DOCUMENTS

| DE | 197 44 131 A1 | 4/1998 |
| DE | 19744131 | 4/1998 |
| EP | 1152687 B1 | 9/2004 |

(Continued)

OTHER PUBLICATIONS

Australian Government, IP Australia, Examiner's First Report on Patent Application No. 2001263366 by Welch Allyn, Inc. dated Dec. 9, 2004, 2 pages.
Australian Government, IP Australia, Examiner's Second Report on Patent Application No. 2001263366 by Welch Allyn, Inc. dated Dec. 19, 2005, 2 pages.
Japanese Patent Office, Examiner's Mailing No. 036153, Notice of Grounds for Rejection dated Jan. 31, 2006 for Japanese Patent Application No. 2000–583418, 3 pages.

(Continued)

*Primary Examiner*—Brandi Thomas
(74) *Attorney, Agent, or Firm*—Marjama & Bilinski LLP

(57) ABSTRACT

There is described in one embodiment an eye viewing device for viewing a structure of an eye such as a retina. The eye viewing device can include an image sensor. In one embodiment an eye viewing device can be adapted to facilitate both visual viewing of an eye structure and electronic image capture.

100 Claims, 15 Drawing Sheets

U.S. PATENT DOCUMENTS

| | | |
|---|---|---|
| 3,698,099 A | 10/1972 | Matsura |
| 3,893,447 A | 7/1975 | Hochheimer et al. |
| 3,914,032 A | 10/1975 | Takano et al. |
| 3,915,564 A * | 10/1975 | Urban ........................ 351/206 |
| 3,925,793 A | 12/1975 | Matsumura et al. |
| 3,936,844 A | 2/1976 | Matsumura |
| 3,944,341 A | 3/1976 | Pomerantzeff |
| 4,023,189 A | 5/1977 | Govignon |
| 4,026,638 A | 5/1977 | Govignon |
| 4,068,932 A | 1/1978 | Ohta et al. |
| 4,095,379 A | 6/1978 | Weintraub |
| 4,102,563 A | 7/1978 | Matsumura et al. |
| 4,106,078 A | 8/1978 | Inoue |
| 4,135,791 A | 1/1979 | Govignon |
| 4,146,310 A | 3/1979 | Kohayakawa et al. |
| 4,149,787 A | 4/1979 | Kobayashi et al. |
| 4,162,827 A | 7/1979 | Ito |
| 4,176,920 A | 12/1979 | Ito |
| 4,184,752 A | 1/1980 | Richards et al. |
| 4,187,014 A | 2/1980 | Kato et al. |
| 4,196,979 A | 4/1980 | Kohayakawa et al. |
| 4,198,144 A | 4/1980 | Matsumura et al. |
| 4,201,456 A | 5/1980 | Wolbarsht |
| 4,227,780 A | 10/1980 | Ohta et al. |
| 4,235,540 A | 11/1980 | Hanamura et al. |
| 4,238,142 A | 12/1980 | Richards et al. |
| 4,247,176 A | 1/1981 | Ito |
| 4,238,506 A | 2/1981 | Takahashi |
| 4,248,505 A | 2/1981 | Muchel et al. |
| 4,249,802 A | 2/1981 | Muchel et al. |
| 4,249,825 A | 2/1981 | Shapiro |
| 4,251,139 A | 2/1981 | Matsumura |
| 4,253,743 A | 3/1981 | Matsumura |
| 4,253,744 A | 3/1981 | Sawa |
| 4,257,688 A | 3/1981 | Matsumura |
| 4,257,691 A | 3/1981 | Brooks |
| 4,264,153 A | 4/1981 | Ito |
| 4,265,518 A | 5/1981 | Matsumura |
| 4,265,519 A | 5/1981 | Pomerantzeff |
| 4,266,861 A | 5/1981 | Sawa |
| 4,279,478 A | 7/1981 | Matsumura |
| 4,283,124 A | 8/1981 | Matsumura |
| 4,318,585 A | 3/1982 | Matsumura |
| 4,329,025 A | 5/1982 | Nishimura et al. |
| 4,331,132 A | 5/1982 | Mukasa |
| 4,365,872 A | 12/1982 | Nunokawa |
| 4,378,147 A | 3/1983 | Fujita |
| 4,400,070 A | 8/1983 | Isono et al. |
| 4,405,215 A | 9/1983 | Sano et al. |
| 4,412,728 A | 11/1983 | Sakane et al. |
| 4,422,735 A | 12/1983 | Shimizu et al. |
| 4,422,736 A | 12/1983 | Nunokawa |
| 4,423,932 A | 1/1984 | Takahashi |
| 4,435,051 A | 3/1984 | Nunokawa |
| 4,436,388 A | 3/1984 | Takahashi et al. |
| 4,436,389 A | 3/1984 | Sano |
| 4,439,023 A | 3/1984 | Iba et al. |
| 4,439,024 A | 3/1984 | Ito |
| 4,449,798 A | 5/1984 | Nohda |
| 4,453,808 A | 6/1984 | Takahashi et al. |
| 4,464,608 A | 8/1984 | Pilley |
| 4,469,416 A | 9/1984 | Isono |
| 4,485,820 A | 12/1984 | Flower |
| 4,502,766 A | 3/1985 | Ito |
| 4,511,227 A | 4/1985 | Nunokawa et al. |
| 4,526,450 A | 7/1985 | Suzuki et al. |
| 4,529,280 A | 7/1985 | Nohda |
| 4,558,932 A | 12/1985 | Nunokawa |
| 4,572,627 A | 2/1986 | Madate et al. |
| 4,580,885 A | 4/1986 | Takahashi |
| 4,591,249 A | 5/1986 | Takahashi et al. |
| 4,613,218 A | 9/1986 | Machida et al. |
| 4,666,264 A | 5/1987 | Yamabe |
| 4,679,919 A | 7/1987 | Itoh et al. |
| 4,690,525 A | 9/1987 | Kobayashi et al. |
| 4,712,894 A | 12/1987 | Nunokawa |
| 4,715,703 A | 12/1987 | Cornsweet et al. |
| 4,715,704 A | 12/1987 | Biber et al. |
| 4,717,952 A | 1/1988 | Kohayakawa et al. |
| 4,721,378 A | 1/1988 | Volk |
| 4,732,466 A | 3/1988 | Humphrey |
| 4,755,043 A * | 7/1988 | Carter ........................ 351/205 |
| 4,755,044 A | 7/1988 | Thorn |
| 4,799,783 A | 1/1989 | Takahashi et al. |
| 4,812,033 A | 3/1989 | Ishikawa |
| 4,824,238 A | 4/1989 | Feldman et al. |
| 4,834,526 A | 5/1989 | Nunokawa |
| 4,856,613 A | 8/1989 | Reginold |
| 4,856,890 A | 8/1989 | Itoh et al. |
| 4,856,891 A | 8/1989 | Pflibsen |
| 4,867,554 A | 9/1989 | Matsumura |
| 4,927,260 A | 5/1990 | Gordon |
| 4,989,023 A | 1/1991 | Sakurai et al. |
| 4,991,584 A | 2/1991 | Kobayashi et al. |
| 4,998,533 A | 3/1991 | Winkelman |
| 5,037,194 A | 8/1991 | Kohayakawa et al. |
| 5,071,245 A | 12/1991 | Fukuma et al. |
| 5,140,352 A | 8/1992 | Moore et al. |
| 5,140,458 A | 8/1992 | Takagi et al. |
| 5,141,303 A | 8/1992 | Yamamoto et al. |
| 5,177,512 A * | 1/1993 | Abe et al. |
| 5,181,055 A | 1/1993 | Sano et al. |
| 5,187,506 A * | 2/1993 | Carter ........................ 351/221 |
| 5,189,556 A | 2/1993 | Ohtsuka |
| 5,214,454 A | 5/1993 | Sano |
| 5,233,372 A | 8/1993 | Matsumoto |
| 5,237,350 A | 8/1993 | Sano |
| 5,237,356 A | 8/1993 | Ohtsuka |
| 5,239,984 A | 8/1993 | Cane et al. |
| 5,247,318 A | 9/1993 | Suzuki |
| 5,255,026 A | 10/1993 | Arai et al. |
| 5,270,747 A | 12/1993 | Kitajima et al. |
| 5,270,749 A | 12/1993 | Okumura |
| 5,270,924 A | 12/1993 | Hideshima |
| 5,287,129 A | 2/1994 | Sano et al. |
| 5,291,231 A | 3/1994 | Hideshima et al. |
| 5,300,964 A | 4/1994 | Kobayashi |
| 5,329,322 A | 7/1994 | Yancey |
| 5,374,967 A | 12/1994 | Hideshima et al. |
| 5,408,264 A | 4/1995 | Kurata et al. |
| 5,420,650 A * | 5/1995 | Kohayakawa ............ 351/206 |
| 5,446,509 A | 8/1995 | Okinishi |
| 5,500,697 A * | 3/1996 | Fujieda ........................ 351/212 |
| 5,523,808 A | 6/1996 | Kohayakawa |
| 5,528,323 A | 6/1996 | Fujieda et al. |
| 5,530,493 A | 6/1996 | Suzuki |
| 5,539,517 A | 7/1996 | Cabib et al. |
| 5,543,865 A | 8/1996 | Nanjo |
| 5,557,321 A | 9/1996 | Kohayakawa et al. |
| 5,565,938 A | 10/1996 | Hanamura et al. |
| 5,572,266 A | 11/1996 | Ohtsuka |
| 5,576,780 A * | 11/1996 | Yancey ........................ 351/211 |
| 5,579,063 A | 11/1996 | Magnante et al. |
| 5,599,276 A | 2/1997 | Hauptli et al. |
| 5,617,156 A | 4/1997 | Sano et al. |
| 5,633,694 A | 5/1997 | Mihashi et al. |
| 5,668,621 A | 9/1997 | Nanjo |
| 5,695,492 A | 12/1997 | Brown |
| 5,742,374 A | 4/1998 | Nanjo et al. |
| 5,745,163 A | 4/1998 | Nakamura et al. |
| 5,757,463 A | 5/1998 | Kohayakawa |

| Patent No. | Date | Inventor |
|---|---|---|
| 5,762,605 A | 6/1998 | Cane et al. |
| 5,764,341 A | 6/1998 | Fujieda et al. |
| 5,914,771 A | 6/1999 | Biber |
| 5,919,130 A | 7/1999 | Monroe et al. |
| 5,993,001 A | 11/1999 | Bursell et al. |
| 5,993,002 A | 11/1999 | Steinhuber |
| 5,995,759 A | 11/1999 | Kohayakawa |
| 6,007,996 A | 12/1999 | McNamara et al. |
| 6,008,781 A | 12/1999 | Furness, III et al. |
| 6,030,080 A | 2/2000 | Ohman |
| 6,065,837 A | 5/2000 | Goldfain et al. |
| 6,075,599 A | 6/2000 | Milman et al. |
| 6,082,859 A | 7/2000 | Okashita et al. |
| 6,116,736 A * | 9/2000 | Stark et al. .................. 351/206 |
| 6,139,151 A | 10/2000 | Ueno et al. |
| 6,142,629 A | 11/2000 | Adel et al. |
| 6,152,565 A * | 11/2000 | Liu et al. ..................... 351/212 |
| 6,158,864 A | 12/2000 | Masuda et al. |
| 6,165,734 A | 12/2000 | Garini et al. |
| 6,193,371 B1 | 2/2001 | Snook |
| 6,196,686 B1 | 3/2001 | Reiner |
| 6,198,532 B1 | 3/2001 | Cabib et al. |
| 6,244,710 B1 | 6/2001 | Ogawa |
| 6,273,565 B1 | 8/2001 | Matsumoto |
| 6,296,358 B1 | 10/2001 | Cornsweet et al. |
| 6,309,625 B1 | 10/2001 | Jensen et al. |
| 6,325,511 B1 | 12/2001 | Mizuochi |
| 6,327,375 B1 | 12/2001 | Matsumoto et al. |
| 6,364,484 B2 | 4/2002 | Yamada |
| 6,390,625 B1 | 5/2002 | Slawson et al. |
| 6,404,985 B1 | 6/2002 | Ohtsuka |
| 6,409,341 B1 | 6/2002 | Goldfain et al. |
| 6,456,787 B1 | 9/2002 | Matsumoto et al. |
| 6,488,377 B2 | 12/2002 | Matsumoto |
| 6,511,420 B1 | 1/2003 | Farrell et al. |
| 6,527,390 B2 | 3/2003 | Goldfain et al. |
| 6,546,198 B2 | 4/2003 | Ohtsuka |
| 6,550,916 B1 | 4/2003 | Sekiguchi |
| 6,574,432 B2 | 6/2003 | Nanjyo |
| 6,575,571 B2 | 6/2003 | Shibata |
| 6,585,374 B2 | 7/2003 | Matsumoto |
| 6,637,882 B1 | 10/2003 | Goldfain et al. |
| D493,528 S | 7/2004 | Roberts et al. |
| D493,887 S | 8/2004 | Roberts et al. |
| 2001/0024263 A1 | 9/2001 | Nanjyo |
| 2001/0028438 A1 | 10/2001 | Matsumoto |
| 2002/0025145 A1 | 2/2002 | Nanjyo |
| 2002/0044257 A1 | 4/2002 | Matsumoto |
| 2002/0047988 A1 | 4/2002 | Matsumoto |
| 2002/0047989 A1 | 4/2002 | Shibata |
| 2002/0067919 A1 | 6/2002 | Shibata et al. |
| 2002/0089643 A1 | 7/2002 | Ogawa |
| 2002/0097379 A1 | 7/2002 | Goldfain et al. |
| 2002/0102099 A1 | 8/2002 | Saito |
| 2002/0113939 A1 | 8/2002 | Kitamura |
| 2002/0158890 A1 | 10/2002 | Ickikawa et al. |
| 2002/0176050 A1 | 11/2002 | Shibata |
| 2003/0025876 A1 | 2/2003 | Nanjo |
| 2003/0035084 A1 | 2/2003 | Makino |
| 2003/0063386 A1 | 4/2003 | Slawson et al. |
| 2003/0068164 A1 | 4/2003 | Nanjyo |
| 2003/0071893 A1 | 4/2003 | Miller et al. |
| 2003/0071966 A1 | 4/2003 | Matsumoto |
| 2003/0076477 A1 | 4/2003 | Matsumoto |
| 2003/0098952 A1 | 5/2003 | Goldfain et al. |
| 2003/0128332 A1 | 7/2003 | Silverbrook et al. |
| 2003/0157464 A1 * | 8/2003 | Tanassi |
| 2003/0208125 A1 * | 11/2003 | Watkins |
| 2004/0119941 A1 | 6/2004 | Goldfain et al. |
| 2005/0110949 A1 | 5/2005 | Goldfain |

FOREIGN PATENT DOCUMENTS

| | | |
|---|---|---|
| JP | 50-147928 | 11/1975 |
| JP | 51-49024 | 4/1976 |
| JP | 52-025494 | 2/1977 |
| JP | 53-126792 | 11/1978 |
| JP | 54-6393 | 1/1979 |
| JP | 55-45216 | 3/1980 |
| JP | 57-148929 | 9/1982 |
| JP | 60-210240 | 10/1985 |
| JP | 61-269108 | 11/1986 |
| JP | 62-500914 | 4/1987 |
| JP | 62-220916 | 9/1987 |
| JP | 63-045295 | 3/1988 |
| JP | 01-150905 | 10/1989 |
| JP | 6-285026 | 10/1994 |
| JP | 7-77658 | 3/1995 |
| JP | 3017433 | 8/1995 |
| JP | 08 317907 | 3/1996 |
| JP | 8317907 | 12/1996 |
| JP | 11-89798 | 4/1999 |
| WO | WO 00/30527 | 6/2000 |
| WO | WO-0189374 A2 * | 11/2001 |
| WO | WO-02087427 A1 * | 11/2002 |

OTHER PUBLICATIONS

Canadian Intellectual Property Office, Requisition by Examier dated Feb. 28, 2006 for Canada Application No. 2,352,148 by Welch Allyn, Inc., 4 pages.

Australian Government, IP Australia, Examiner's Third Report on Patent Application No. 2001263366 by Welch Allyn, Inc. dated Mar. 17, 2006, 2 pages.

U.S. Design Pat. Appl. No. 29/207,233 filed Jun. 10, 2004, Fitch et al.

www.Delphion.com, Internet Search of US20020097379A1: Eye Viewing Device Comprising Eyepiece and Video Capture Optics, "Patent Family" Internet Seach Dated October 27, 2004 (4 pages). Reference summarizes data.

[Continuation of description of reference "AO"]. . . identifying US and Foregin patent references related to the present application.

Express Abandonment Under 37 CFR 1.138, dated Jan. 12, 2005, submitted in U.S. Pat. Appl. No. 10/671,645, filed Sep. 25, 2003. Also, an Express Abandonment Remarks Amendment.

JP Patent Application 2000–583418 Notice of Grounds for Rejection in the English language.

International Search Report PCT/US2004/035799, Dated Mar. 22, 2005.*

International Search Report PCT/US2004/035799, Dated Mar. 22, 2005, 4 pages.

Office Action for U.S. Pat. Appl. No. 10/976,029 Dated Feb. 22, 2007, 10 pages.

* cited by examiner

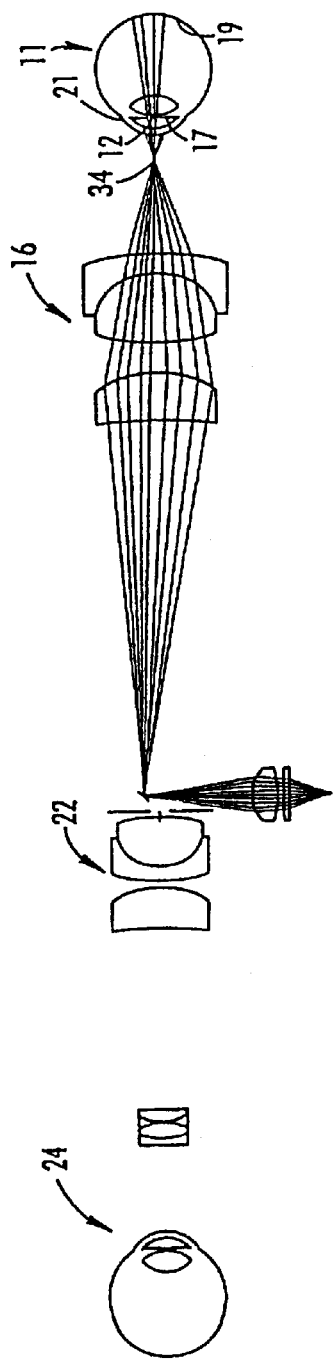
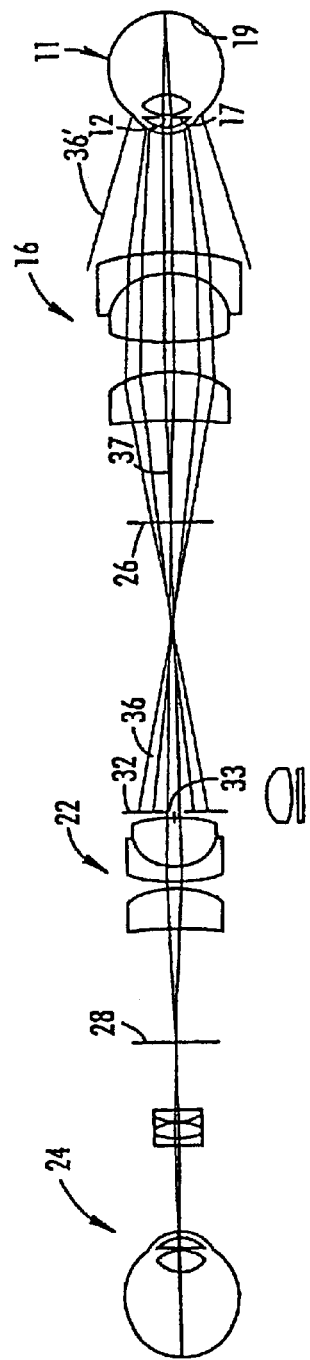
FIG. 1c
FIG. 1d

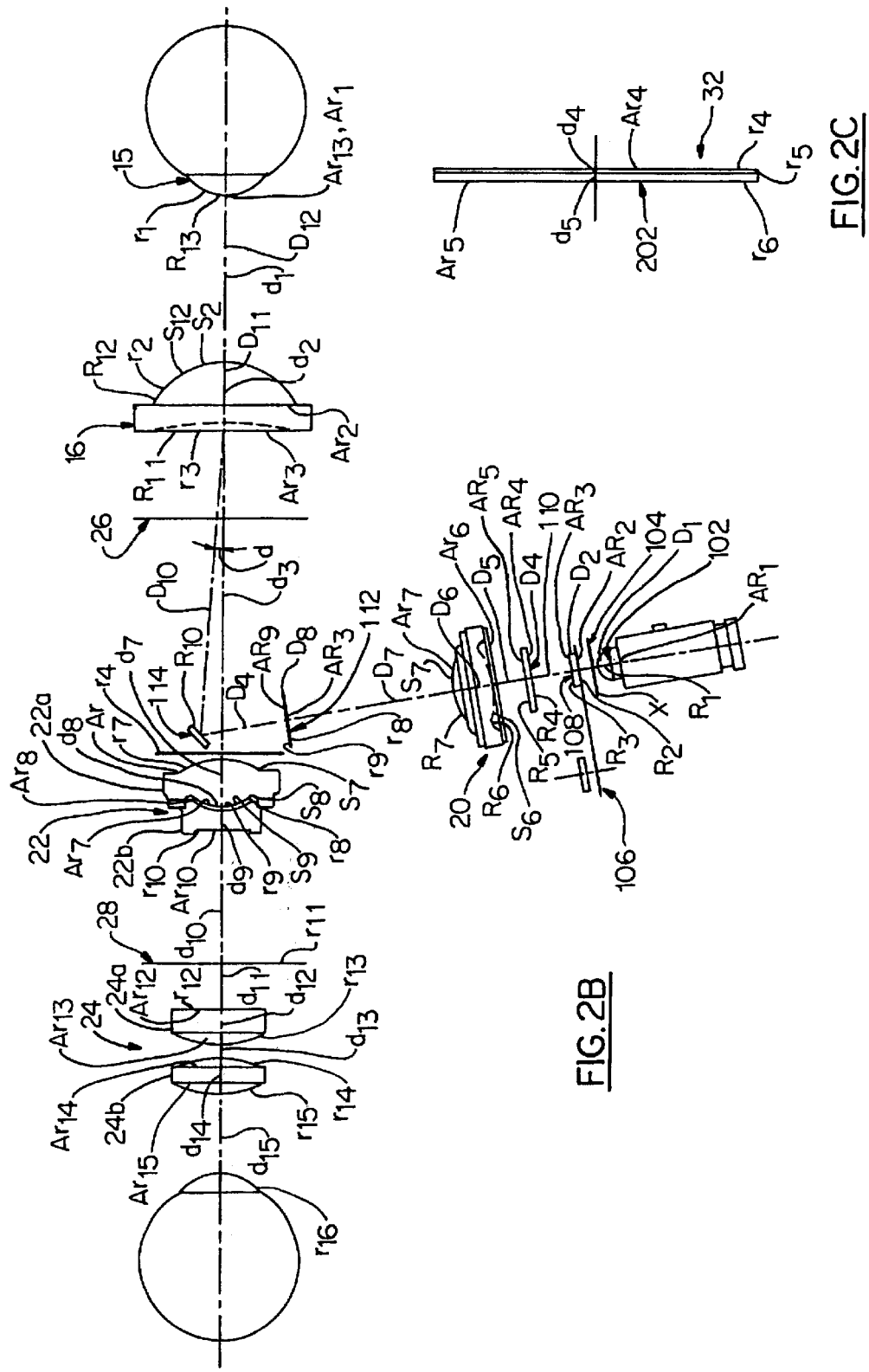

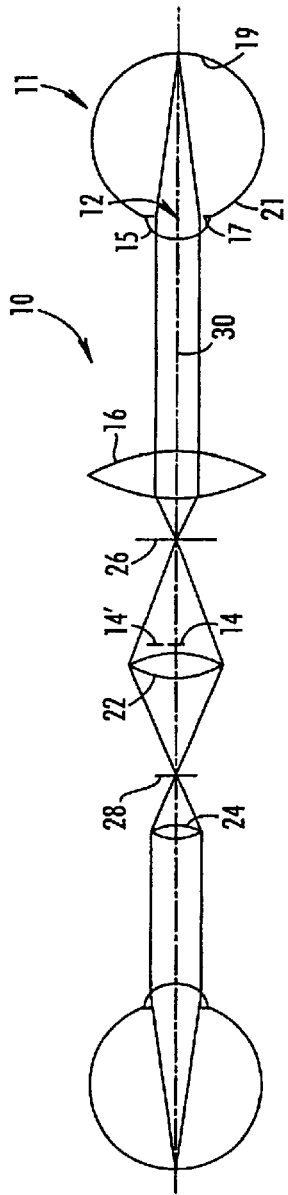
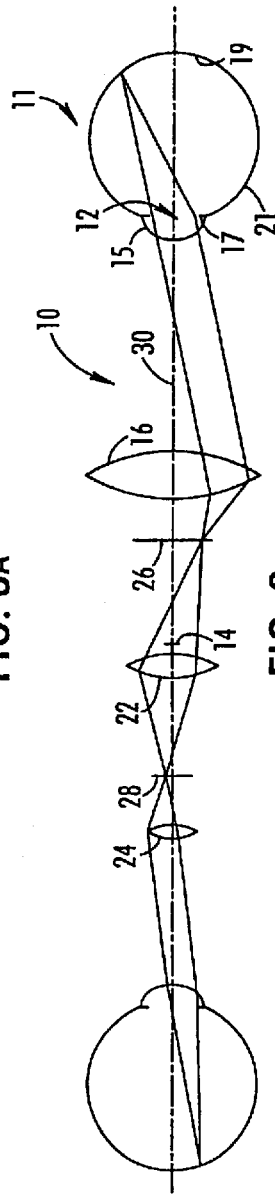
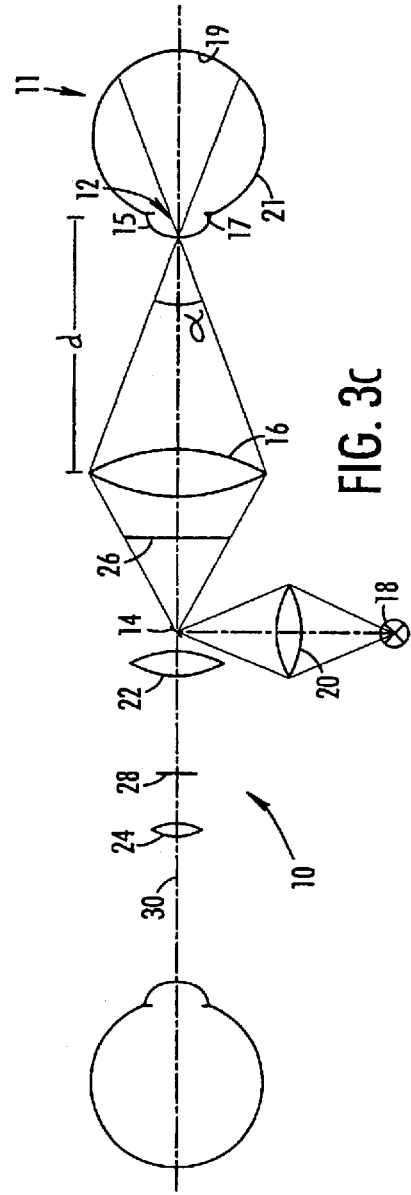
FIG. 3A
FIG. 3B
FIG. 3c

EYE VIEWING DEVICE COMPRISING EYEPIECE AND VIDEO CAPTURE OPTICS

CROSS REFERENCE TO RELATED APPLICATIONS

Reference is made to and priority claimed from U.S. Provisional Application Serial No. 60/206,356 entitled "Eye Viewing Device for Retinal Viewing Through Undilated Pupil" filed May 23, 2000. This application is also a continuation-in-part of application No. 09/783,481 entitled "Eye Viewing Device for Retinal Viewing Through Undilated Pupil" filed Feb. 14, 2001, which is a continuation-in-part of application No. 09/444,161 entitled "Eye Viewing Device for Retinal Viewing Through Undilated Pupil" filed Nov. 22, 1999, which is a continuation-in-part of application No. 09/198,545 entitled "Ophthalmoscope Comprising Defocused Light Source" filed Nov. 24, 1998, which issued May 23, 2000 as U.S. Pat. No. 6,065,837. The priorities of the above applications are claimed and the above applications are incorporated herein by reference.

BACKGROUND OF THE INVENTION

1. Field of the Invention

This invention relates generally to medical diagnostic instruments, and specifically to an eye viewing device for use in retinal viewing.

2. Background of the Prior Art

Commercially available eye viewing devices for use in retinal viewing have been observed to exhibit numerous limitations.

According to an indirect ophthalmoscope design, a beam splitter is provided in the optical viewing path which directs illumination light rays into an eye, and simultaneously allows receive imaging light rays to pass therethrough. The substantial light losses inherent with this design require that a large, high powered light source be incorporated in the device for the device to satisfactorily illuminate a retina. High powered light sources, in general, are difficult to package, consume excessive amounts of electrical input power, and produce large amounts of heat and unwanted light such as glare. High powered light sources also have large filaments, typically larger than the diameter of an undilated pupil. This makes indirect ophthalmoscopes especially susceptible to glare problems attributable to incident light rays being reflected from outer eye structures such as the iris, cornea and sclera.

Cameras for use in retinal viewing, such as fundus cameras, provide high quality imaging. However, retinal viewing cameras, in general, are expensive, typically require pupil dilation for retinal viewing, and typically require operation by a highly skilled and trained camera operator and these cameras are also large, bulky, and consume excessive space. Because present retinal viewing cameras are fixed position cameras, they require that a patient move into a certain position relative to the camera for an operative position to be achieved.

There is a need for a compact, lower input power eye hand-held viewing device which provides appropriate retinal illumination, which facilitates wide field retinal viewing without requiring pupil dilation, and which can be adapted for use in capturing images corresponding to eye structures.

SUMMARY OF THE INVENTION

According to its major aspects and broadly stated, the present invention is a low input power, low cost eye viewing device for use in viewing a retina.

There is described in one embodiment an eye viewing device for viewing a structure of an eye such as retina. The eye viewing device can include an image sensor. In one embodiment an eye viewing device can be adapted to facilitate both visual viewing of an eye structure and electronic image capture.

These and other features of the invention will become clear to those skilled in the art from a careful reading of the Detailed Description of the Preferred Embodiments in connection with the referenced drawings.

BRIEF DESCRIPTION OF THE DRAWINGS

The preferred embodiment of the invention will now be described by way of example only, with reference to the accompanying figures wherein the elements bear like reference numerals, and wherein:

FIG. 1C is a functional schematic diagram of an eye viewing device of the invention showing incident illumination light rays when the device is at a distance away from an operative position;

FIG. 1D is a functional schematic diagram of the eye viewing device of FIG. 1C showing receive optical light rays when the device is at a distance away from an operative position;

FIG. 2B is a schematic diagram illustrating a specific embodiment of the invention;

FIG. 2C is an exploded view of a section of the specific embodiment shown in FIG. 2A.

FIG. 3A is a functional schematic diagram of an embodiment of the invention showing light rays from an on-axis object illustrating operation of an embodiment of an imaging system according to the invention having a defocused mirror;

FIG. 3B is a functional schematic diagram of an embodiment of the invention showing light rays from an off-axis object illustrating operation of an imaging system according to the invention having a defocused mirror;

FIG. 3C is a functional schematic diagram of an embodiment of the invention showing illumination light rays which illustrate operation of an illumination system having an on-axis light source;

DETAILED DESCRIPTION OF THE INVENTION

Figure 1A:
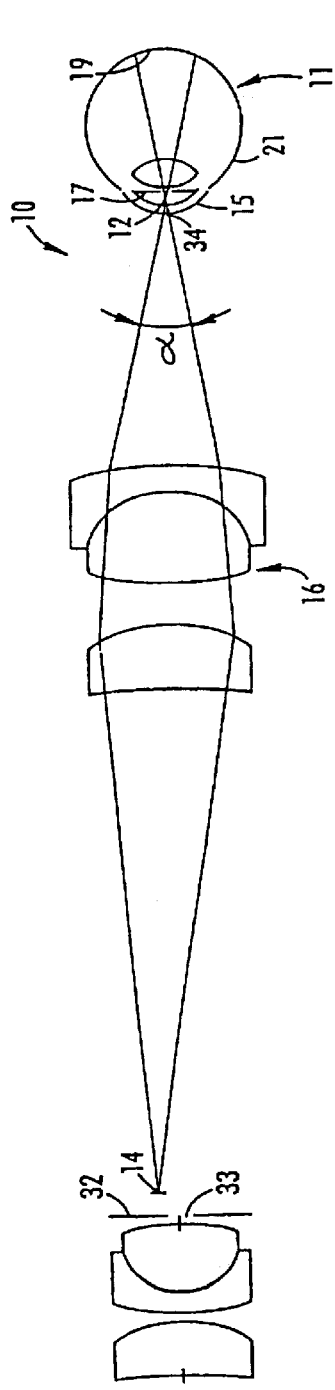
FIG. 1A is a functional schematic diagram of an eye viewing device of the invention showing illumination light rays for illustrating operation of an illumination system according to the invention.

In one aspect of the invention, the illumination and imaging assemblies of the invention are at least partially disposed in a housing, and formed at an observer end of the housing is a holder which replaceably receives a viewing module. The viewing module replaceably received by the earpiece optics elements holder of the housing may comprise eyepiece optics, image signal generating elements, or combined eyepiece optics and image signal generating elements.

In one aspect, an eye viewing device according to the invention includes a converging light illumination system adapted to generate light rays which, when the device is an operative position, converge at about a pupil of a patient and diverge inside an eye to illuminate a wide retinal field. The converging light illumination system provides illumination of a wide retinal field through a small pupil which may be in an undilated state. The converging light illumination system also reduces electrical input power consumption and reduce glare, as substantially all light delivered by the illumination system enters an eye through a patient's pupil without being reflected from an eye structure outside of a pupil opening such as the iris and sclera.

In another aspect, an eye viewing device of the invention includes a viewing system having an aperture stop positioned substantially conjugate to a patient's pupil and substantially coaxial with an imaging axis of the viewing system. An aperture stop positioned substantially conjugate to a patient's pupil and substantially coaxial with an imaging axis operates to admit light that forms a retinal image and to block light that does not form the retinal image. The aperture stop operates to block unwanted light both when the device is positioned forward of an operative position and when the device is in an operative position. The aperture stop thereby reduces glare and improves image quality both during entry of the device into an eye (when the device is being maneuvered into an operative position) and during retinal viewing (when the device is in an operative position).

The eye viewing device is made especially well suited for retinal viewing through an undilated eye by sizing the aperture of the aperture stop in accordance with the diameter of a pupil of an indilated eye. By sizing the aperture in accordance with the diameter of an undilated pupil, the aperture stop operates to block substantially all light reflected from eye structures outside the diameter of a pupil (such as the iris and sclera).

The above optical elements working in combination provide for wide field retinal viewing without pupil dilation.

Additional aspects of an eye viewing device are described in U.S. Patent Publication No. 2002/0097379 entitled, "Eye Viewing Device Comprising Eyepiece And Video Capture Optics," filed May 22, 2001, incorporated herein by reference.

An exemplary embodiment of an eye viewing device according to the invention is described with reference to FIGS. 1A–1E. Eye viewing device 10 includes an illumination system, the operation of which is described mainly with reference to FIG. 1A, and an imaging system, the operation of which is described mainly with reference to FIG. 1B.

The device of FIGS. 1A–1E is especially well suited for use in viewing a retina through an undilated pupil. Small diameter undilated pupils present numerous challenges to viewing retinal images. Small diameter undilated pupils tend to inhibit the transmission of both incident light directed toward a retina and reflected light corresponding to a retinal image. Furthermore, light that is directed into a pupil and that is blocked from entry into a pupil by highly reflective surfaces of outer eye structures such as the iris and sclera tends to be reflected into a viewing system as glare. As will be explained herein below, the device of FIGS. 1A–1E includes features which operate in combination to overcome the numerous challenges to viewing a retinal image through an undilated pupil. In one aspect, the device of FIGS. 1A–1E includes the combination of a converging light source illumination system and an aperture stop. The converging light source illumination system operates to direct a substantial amount of light through a small diameter opening while the aperture stop operates to block glare attributable to light rays being reflected from outer eye structures.

As best seen by FIG. 1A, the illumination system operates to generate illumination light rays which converge at an apex 34 and diverge thereafter. An eye viewing device having a converging light ray illumination system is positioned in an operative position relative to a patient when substantially a maximum amount of incident light enters eye 11 through pupil 12. In the device of FIG. 1A–1E, an operative position is achieved when apex 34 of the cone of light generated by the illumination system is positioned at about a pupil 12 of a patient. With a converging light ray illumination system, a substantial amount of illumination light enters a small diametered pupil and at the same time illuminates a wide retinal field. A converging light ray illumination system can be provided by the combination of a light source 14 and objective lens 16 positioned forward of the light source 14 for converging light rays emanating from source 14. With a converging light source illumination system, a much higher percentage of incident light rays enter pupil 12 to illuminate retina 19 than are reflected off outer eye structures 17 and 21. Because there is little wasted incident light, a converging light ray illumination system reduces the electrical input power consumption of the illumination system. Because a relatively smaller amount of incident light reflects off outer eye structures such as iris 17 and sclera 21, there is less unwanted light received by the imaging system.

Figure 2A:
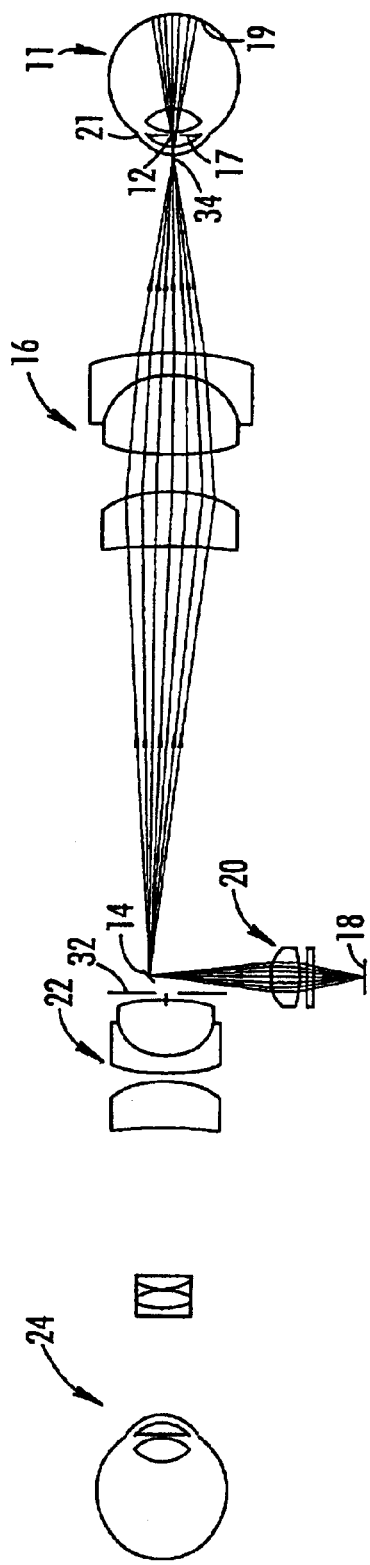
FIG. 2A is a functional schematic diagram showing incident light rays of an illumination system which may be incorporated in the invention.

Light source 14 can be a light generating light source, such as a filament-based lamp, an arc lamp, a fiber optic light source or a solid state light source. However, with presently available technology, light generating light sources are sufficiently large that they introduce packaging problems. Therefore, a preferred light source for the eye viewing device is the light source described with reference to FIG. 2A. In the embodiment of FIG. 2A, light source 14 is provided by a reflective element such as a mirror, which operates in association with a light-generating light source 18, such as a lamp, and a condenser lens 20 which converges light from light source 18 onto mirror 14.

Aspects of the imaging system of the device will now be described with reference mainly to FIG. 1B. The imaging system of the device includes objective lens 16, imaging lens 22, and an eyepiece lens 24. A retinal image focal plane 26 is produced intermediate objective lens 16 and imaging lens 22, while an eyepiece focal plane 28 is produced intermediate imaging lens 22 and eyepiece lens 24. The imaging system further includes an imaging axis 30 on which lenses 16, 22, and 24 are substantially centered. In all references herein, the term "lens" can refer to a single optical element or a plurality of optical elements functioning together, while an operative position has been defined herein as the position at which substantially a maximum amount of incident light rays enter eye 11 through pupil 12. An operative position can also be defined as the position at which a patient's pupil is conjugate to aperture stop 32.

The retinal image light rays crossing retinal focal plane 26 consist of light rays that enter eye 11 through pupil 12 and which are reflected from retina 19 through pupil 12. Since small undilated pupils tend to inhibit the transmission of both incident light into an eye and reflected retinal image light out of the eye, retinal images viewed through undilated pupils are readily obscured by glare (which is especially prevalent when retinas are viewed through undilated pupils since incident light is more likely to be reflected from highly reflective outer eye structures). In addition to glare attributable to light being reflected from outer eye structures, retinal images can be obscured by glare attributable to other sources such as light that is reflected from a patient's cornea (corneal glare) and light that is reflected from a component of the eye viewing device such as a lens of the device (internal glare).

To the end that the device is well adapted for viewing retinal images through an undilated pupil, device 10 preferably includes features which operate to reduce such glare, and in so doing reduce the percentage of received light rays not corresponding to a retinal image relative to the percentage of received light rays corresponding to a retinal image.

One feature which operates to reduce the percentage of light rays not corresponding to the retinal image is the feature of converging light illumination, described above. In a converging light illumination system, a relatively high percentage of light enters eye 11 through pupil 12, and a relatively low percentage of light is reflected from outer eye structures 17 and 21 as seen in FIG. 1A. Other features which may be incorporated to increase the percentage of retinal image forming received light relative to unwanted light are described herein below.

Figure 1B:
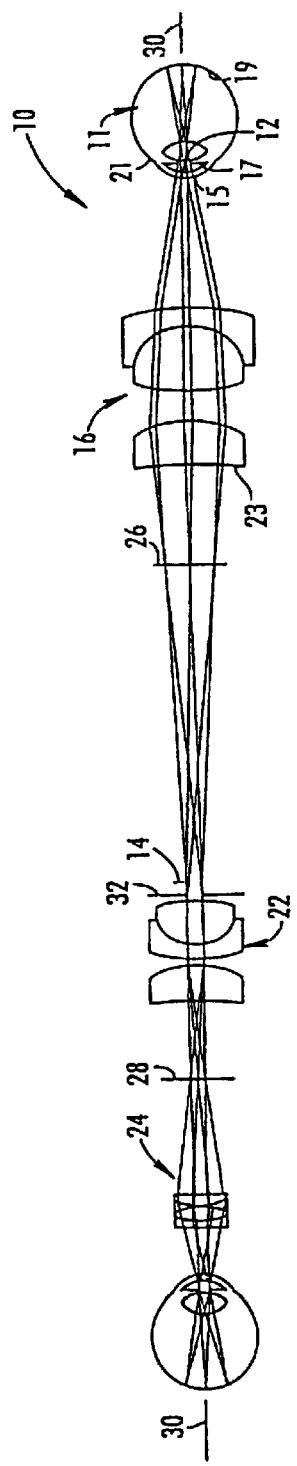
FIG. 1B is a functional schematic diagram of an eye viewing device of the invention showing receive optical light rays which illustrate operation of the device's imaging system.

In the device of FIG. 1B, an aperture stop 32 is positioned forward of imaging lens 22 to block unwanted light. Aperture stop 32 should be positioned substantially coaxially with imaging axis 30 and substantially conjugate to a patient's pupil 12 when in an operative position in relation to device 10. Positioning of aperture stop 32 substantially coaxial with imaging axis 30 encourages substantially a maximum amount of useful receive imaging light to be admitted through imaging lens 22 without also admitting glare light that originates radially outside the patient's pupil 12. By positioning aperture stop 32 so that it is substantially conjugate to a pupil, aperture stop 32 operates to block light reflected from outer eye structures 17 and 21. Because the apex 34 of the cone of light generated by illumination system is substantially conjugate to a patient's pupil for positioning the device in an operative position, and because the preferred position of aperture stop is also one that is conjugate to the pupil, then the preferred position of aperture stop 32 in a device made in accordance with FIGS. 1A–1E can be described as one that is substantially conjugate to the apex of the cone of light generated by the illumination system.

For optimal blocking of unwanted received light, aperture 33 of aperture stop 32 should be sized in accordance with the diameter of the pupil through which a retina is viewed. The diameter of an undilated pupil is about 2 mm. Accordingly, for optimally configuring device 10 for viewing a retina through an undilated pupil, aperture 33 should be sized to correspond to a patient pupil diameter of about 2 mm. The resulting diameter of aperture 33 is determined by multiplying the pupil diameter by the magnification of the pupil in the plane of the aperture stop 32. This same principle can be applied to optimize the instrument design for other pupil sizes, larger and smaller.

In addition to reducing glare and improving image quality when device 10 is in an operative position, aperture stop 32 reduces glare and improves image quality prior to the device being moved into an operative position. FIGS. 1C and 1D illustrate illumination light rays exiting the device and reflecting off the eye as they are received in a viewing system of device 10 during entry of the device into an eye (during the process of moving the device into an operative position). FIG. 1C illustrates incident light rays generated by device 10 when the device is at a distance away from an operative position, while FIG. 1D illustrates received reflected light rays of a device positioned at the same distance away from an operative position as is shown in FIG. 1C. It is seen that when the device is away from an operative position, then light rays generated by the illumination system strike eye 11 in a diverged state (apex 34 of the cone of light is positioned forward of pupil 12). Thus, a relatively small percentage of incident rays enter an eye through pupil 12 and a relatively high percentage light rays are reflected from the highly reflective outer surfaces of eye structures such as iris 17 and sclera 21. Light rays reflected from outer eye structures 17 and 21 tend to be reflected at an angle with respect to imaging axis 30. The curved surface of eye 11 assures that reflected light rays are reflected at an angle with respect to axis 30. When device 10 is a substantial distance away from an operative position many light rays reflected from eye 11 during entry of the device are reflected out of the viewing system entirely as is indicated by rays 36. The majority of light rays that are received in the viewing system are blocked by aperture stop 32 as is indicated by rays 36. Only a small percentage of light rays such as rays 37 pass through aperture 33. Light rays that pass through aperture 33 consist of rays that originated as incident light rays directed substantially along axis 30 and that passed through pupil 12 to retina 19. Thus, during entry of device 10 into eye 11, it can be seen that aperture stop 32 tends to block unwanted light and to pass light corresponding to a retinal image.

It will be seen that without aperture stop 32, a substantial majority of light rays transmitted to eyepiece focal plane 28 during entry would be light rays reflected from outer eye structures 17 and 21. Thus, the image received at eyepiece focal plane 28 would be heavily obscured by glare. With aperture stop 32 the substantial majority of light rays received at eyepiece focal plane correspond to retina 19. During entry into the eye, the user will see a small field image of the retina, known as the "red reflex" which helps an operator move the device into an operative position without significant glare. By maintaining the retinal image spot near the center of eyepiece focal plane 28 and moving the device toward an eye 11, an operative position can easily be achieved.

Additional glare or unwanted light reducing features may be incorporated in the device. As is shown in FIGS. 1A–1E, light source 14 may be positioned just forward of aperture stop 32 outside of the boundary between received and blocked light and off-axis with respect to imaging axis 30 of device 10. Positioning light source forward of aperture stop 32, outside of the boundary between received and blocked light defined by aperture 33, assures that light source 14 has no obscuring effect on the viewed image and assures maximum image brightness in the user's eye. Positioning light source 14 off-axis also reduces both internal and corneal glare. By positioning light source off-axis, incident light that is reflected off of lens 16 or off of cornea 15 is directed at an angle with respect to axis 30 and, therefore, away from the optical receive path.

Figure 1E:
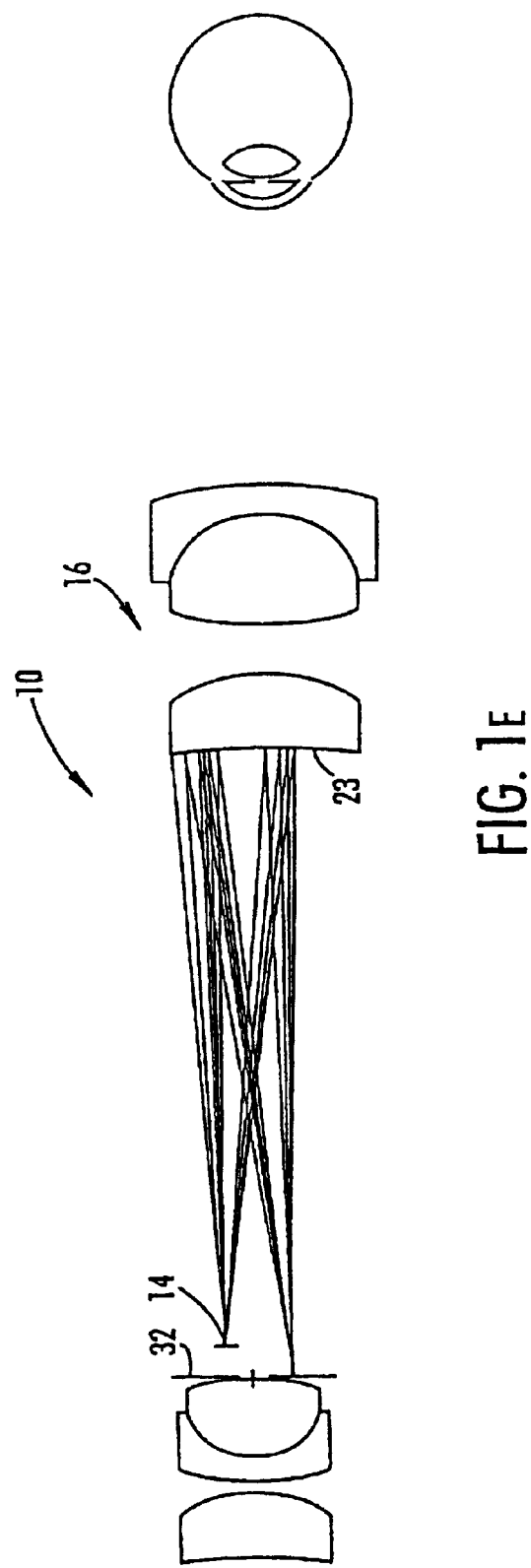
FIG. 1E is a functional diagram of an eye viewing device of the invention showing incident light rays reflected from an objective lens.

Glare may be further reduced by shaping the first surface 23 of objective lens 16 so that first surface 23 is curved and substantially concentric with the center of aperture 33 as seen by the embodiment of FIG. 1E. This assures that light that is reflected from surface 23 is reflected to a point equal to and opposite light source 14 with respect to imaging axis 30. If light source 14 is positioned outside of the boundary dividing blocked and received light defined by aperture 33, the concentric curved first surface 23 assures that internal glare resulting from light being reflected from surface 23 is blocked by aperture stop 32.

In addition to the above features reducing unwanted received light, glare can be reduced by disposing linear polarizers in the imaging and illumination paths in a crossed configuration.

A specific embodiment of an eye viewing device described generally with reference to FIGS. 1A–2A is described with reference to the physical layout diagram of FIG. 2B. This embodiment is advantageous compared to that in FIG. 2A because fewer number of lenses are used and because the non-eyepiece lenses are made from inexpensive molded plastic. The surfaces of the various elements of the illumination system of the eye viewing device of FIG. 2B are numbered surfaces 100 through 113. The elements containing these surfaces are briefly described herein below.

Referring to elements of the embodiment of FIG. 2B in greater detail, lamp filament 102 provides the source of illumination for the illumination system. In the embodiment of FIG. 2B, light source 102 preferably comprises a filament having a length of about 0.025 to 0.030 inches, a diameter of between about 0.0123 and 0.0136 inches, a number of turns of between 6.5 to 7.5, and a power rating of between approximately 3.25 and 3.33 watts. Lamp filament 102 is preferably oriented horizontally and rotated about 90° from the viewing axis.

Device 10 may have an aperture window 104 that lies in plane X. In the case that device 10 includes an aperture window that lies in plane X, the aperture window should be formed at a position that is conjugate to a patient's retina. A smaller aperture provides easier view of a patient's retina through small pupils and cataracts. A larger aperture may be used for dilated pupils and for general examination of the central and peripheral retina.

Device 10 further includes an aperture wheel 106 comprising a plurality of optical elements which may be rotated into a position forward of filament 102 in the illumination optical path. Aperture wheel 106, for example, may carry an apertured glass 108. Apertured glass 108 may comprise plate glass having a lithography-formed slit or a machined slit in a metal substrate. The slit is helpful in determining various levels of retinal lesions, particularly tumors and edematous optic discs.

Apertured glass 108 may further comprise light filtering material. Preferably, apertured glass 108 filters red light and blue light. The red-free filter excludes red retinal rays for easy identification of veins, arteries, and nerve fibers. The blue filter is used in conjunction with fourescein drops applied to the eye to detect corneal abrasions and other anterior and posterior segment lesions. Spacing apertured glass 108 a distance away from plane X minimizes the imaging of surface imperfections onto a retina. The illumination system shown in FIG. 2B further includes wide band hot mirror 110 which limits infrared and UV energy from entering a patient's eye.

Referring to further components of the illumination system of FIG. 2B, the illumination system includes condenser lens 20, which as described previously collects light from filament 102 and operates in combination with objective lens 16 to project an image of filament 102 onto or near a patient's cornea.

The illumination system shown in FIG. 2B further includes linear polarizer 112. As will be described further herein, linear polarizer 112 operates in combination with linear polarizer 202 of the imaging system to reduce corneal glare and glare that originates from the objective lens.

In the specific embodiment of the invention shown in FIG. 2B light source 14 is reflected by mirror 114. The magnification of filament 102 onto mirror 114 is about 1.5 in the embodiment shown. Mirror 114 is mounted at an angle, $\alpha$, of 3.8 degrees from imaging axis 30 relative to objective lens 16. The orientation of the filament matches the geometric shape of the mirror, thus minimizing the mirror size.

Objective lens 16 operates in combination with condenser lens 20 to project an image of filament 102 onto a patient's cornea 15. Objective lens 16 and cornea 15 also form part of the imaging system.

Referring now to elements of the imaging system, retinal image light rays pass through cornea 15 in a collimated formation. Objective lens 16 focuses the parallel light from the patient's eye to a retinal image focal plane 26 between the objective lens and aperture stop 32, FIG. 2C.

Aperture stop 32 operates to block light that originates outside a 2 mm diameter circle located about 25 mm from the objective lens. This is the location of a patient's pupil when the instrument is in its nominal operating position.

Linear polarizer 202, as alluded to previously, operates in combination with linear polarizer 112 of the illumination system to reduce internal and external glare, especially internal glare from the objective lens and external glare attributable to corneal reflections. Linear polarizer 112 of the illumination system and linear polarizer 202 of the imaging system are disposed in a cross-polarized configuration.

Imaging lens 22 in the embodiment of FIG. 2B includes two lens elements, a first lens element 22A and second lens element 22B. The lens elements forming the imaging lens are separated by an air gap. Imaging lens 22 images the retinal image focal plane 26 of the objective lens 16 to the eyepiece focal plane 28.

A field stop (not shown) sized to correspond to the field of view may be disposed at eye piece plane 28. Retinal image focal plane 26 and eyepiece focal plane 28 are conjugate to the patient's and viewer's retinas. Two internal image planes are required for proper orientation of the user's view of the patient's retina eyepiece lens 24 not labeled in FIG. 2b.

Eyepiece lens 24 comprises two lens elements 24A and 24B. The eyepiece assembly in the embodiment of FIG. 2B has an approximately +/−18 diopter focusing range. An apparatus for use in moving eyepiece lens elements 24A and 24B is described in commonly assigned copending application Ser. No. 09/774,726 entitled "Focusing Mechanism" filed Jan. 31, 2001 and incorporated herein by reference.

All of the lenses of the illumination system and imaging system described herein above should be coated with an anti-reflection coating.

Table 1 shows the value of the radius of curvature R (in mm), the on-axis surface spacing D (in mm), the aperture radius, AR, as well as the material associated with each optical surfaces of the specifically designed illumination system shown in FIG. 2B. The six-digit numbers in the "materials" column of Table 1 and Table 3 refer to military code material identifications.

TABLE 1

| Radius | Thickness | Aperture Radius | Material |
|---|---|---|---|
| $R_1 = \infty$ | | $AR_1 = 0.381000$ | |
| | $D_1 = 4.656$ | | Air |
| $R_2 = \infty$ | | $AR_2 = 1.105$ | |
| | $D_2 = 1.000000$ | | 523586 |
| $R_3 = \infty$ | | $AR_3 = 1.105$ | |
| | $D_3 = 6.120$ | | Air |
| $R_4 = \infty$ | | $AR_4 = 3.250$ | |
| | $D_4 = 1.000000$ | | 523586 |
| $R_5 = \infty$ | | $AR_5 = 3.250$ | |
| | $D_5 = 4.800$ | | Air |
| $R_6 = 10.213177$ | | $AR_6 = 5.500$ | |
| | $D_6 = 6.000000$ | | Acrylic |
| $R_7 = -11.362687$ | | $AR_7 = 5.500$ | |
| | $D_7 = 24.630$ | | Air |
| $R_8 = \infty$ | | $AR_8 = 2.000$ | |
| | $D_8 = 0.280000$ | | Polarizer |
| $R_9 = \infty$ | | $AR_9 = 2.000$ | |
| | $D_9 = 12.620$ | | Air |
| $R_{10} = \infty$ | | $AR_{10} = 1.350000$ | |
| | $D_{10} = 46.600000$ | | Air |
| $R_{11} = -46.500000$ | | $AR_{11} = 10.300000$ | |
| | $D_{11} = 9.500000$ | | Acrylic |
| $R_{12} = -8.509000$ | | $AR_{12} = 10.300000$ | |
| | $D_{12} = 26.500$ | | Air |
| $R_{13} = \infty$ | | $AR_{13} = 1.000$ | |

Table 2 shows the coefficients characterizing the rotationally symmetric aspheric surfaces $S_5$, $S_6$, and $S_{12}$ of the specific illumination system shown in FIG. 2B. Rotationally symmetric aspheric surfaces are defined by:

$$z = \frac{cvY^2}{1 + (1 - cv^2(cc+1)Y^2)^{1/2}} + adY^4 + aeY^6 + afY^8 + agY^{10} \qquad \text{Equation 1}$$

where
CC=The Conic Constant
R=Radius of curvature
cv=1/R
Y is the radial distance from the optical axis, and
Z is the sag of the surface
ad, ae, af, ag=higher order aspheric coefficients

TABLE 2

| surface | cc | ad | ae | af | ag |
|---|---|---|---|---|---|
| $S_6$ | -3.224406 | 0 | 0 | 0 | 0 |
| $S_7$ | -2.037497 | 0 | 0 | 0 | 0 |
| $S_{12}$ | -2.427960 | -0.000246 | 5.3906e-07 | 5.1989e-09 | -2.8038e-11 |

Table 3 shows the values of the radius of curvature R (in mm), the on-axis surface spacing d (in mm), the aperture radius, Ar, as well as the material composition associated with each optical surface of the specifically designed imaging system shown in FIG. 2B.

TABLE 3

| Radius | Thickness | Aperture Radius | Material |
|---|---|---|---|
| $r_1 = \infty$ | | $Ar_1 = 1.0000$ | |
| | $d_1 = 26.5$ | | Air |
| $r_2 = 8.509485$ | | $Ar_2 = 10.300000$ | |
| | $d_2 = 9.50000$ | | Acrylic |
| $r_3 = 46.500000$ | | $Ar_3 = 10.300000$ | |
| | $d_3 = 49.040000$ | | Air |
| $r_4 = \infty$ | | $Ar_4 = 1.6000$ | |
| | $d_4 = 0.130000$ | | Metal Aperture Stop |
| $r_5 = \infty$ | | $Ar_5 = 3.5000$ | |
| | $d_5 = 0.280000$ | | Polarizer |
| $r_6 = \infty$ | | $Ar_6 = 9.526$ | |
| | $d_6 = 0.550000$ | | Air |
| $r_7 = 8.754023$ | | $Ar_7 = 3.500000$ | |
| | $d_7 = 6.350000$ | | Acrylic |
| $r_8 = -3.91996$ | | $Ar_8 = 3.500000$ | |
| | $d_8 = 0.450000$ | | Air |
| $r_9 = -4.389902$ | | $Ar_9 = 3.000000$ | |
| | $d_9 = 3.000000$ | | Styrene |
| $r_{10} = -69.717470$ | | $Ar_{10} = 3.500000$ | |
| | $d_{10} = 20.879000$ | | Air |
| $r_{11} = 6.6400$ | | $Ar_{11} = 4.085$ | |
| | $d_{11} = 6.6400$ | | Air |
| $r_{12} = -90.422$ | | $Ar_{12} = 6.000000$ | |
| | $d_{12} = 5.000000$ | | 699301 |
| $r_{13} = -16.490875$ | | $Ar_{13} = 6.000000$ | |
| | $d_{13} = 2.00000$ | | Air |
| $r_{14} = 19.000000$ | | $Ar_{14} = 6.000000$ | |
| | $d_{14} = 5.000000$ | | 517642 |
| $r_{15} = -19.000000$ | | $Ar_{15} = 6.000000$ | |
| | $d_{15} = 12.500000$ | | Air |
| $r_{16} =$ | | $Ar_{16} = 2.763278$ | |

Table 4 shows the coefficients characterizing the rotationally symmetric aspheric surfaces $s_2$, $s_7$, $s_8$, and $s_9$ of the specific imaging system of FIG. 2A as defined by equation

TABLE 4

| surface | cc | ad | ae | af | ag |
|---|---|---|---|---|---|
| $s_2$ | -2.427960 | 0.000246 | -5.3906e-07 | -5.1989e-09 | 2.8038e-11 |
| $s_7$ | -2.799230 | 1.9656e-05 | 4.5561e-06 | -3.9069e-06 | -1.7903e-08 |
| $s_8$ | -1.816998 | 5.9368e-06 | -3.6825e-05 | -5.7481e-06 | 7.1492e-07 |
| $s_9$ | -2.113129 | -0.000142 | -3.3190e-05 | -9.9715e-06 | 2.8898e-06 |

As is well known, the dimensions designated in Tables 1–4 can be scaled up or down. Furthermore, while the dimensions designated in Tables 1–4 pertain to one preferred embodiment of the invention, it will be understood that the components of the eye viewing device may bear relationships to one another that deviate from those listed in Tables 1 to 4. In developing guidelines for the manufacture of alternative embodiments of the eye viewing device having the general configuration shown in FIGS. 1A–2B, the inventors have found that it is advantageous to maintain certain dimensions of the system and relationships between certain components of the system within certain ranges. Specifically, with respect to the embodiment shown in FIGS. 2B and 2C, relationships described hereinbelow apply.

Referring to features of the illumination system, the inventors have found it advantageous to maintain the focal length of the condenser lens 20 between about 8 mm and 15 mm, and to maintain the magnification of the filament onto mirror between about 1 and 2. As has been explained with reference to FIG. 1E, internal glare is reduced by shaping the concave surface of objective lens 16 so that the concave surface is substantially centered about the center of aperture stop 32. The inventors have found the glare-reducing benefits of such a configuration are substantially yielded if the radius of the concave surface and the distance from the center of the aperture stop to the concave lens surface differ by approximately less than 10 percent. length of imaging lens 22 should be maintained between about 10 mm and 20 mm. The inventors have also found that imaging lens 22 preferably operates in a reduction mode with a magnification of between about 0.5 and about 0.9.

The optical elements described with reference to FIG. 2B herein may be housed in a housing such as a housing shown in one of the commonly assigned Design patent application Nos. 29/137,181; 29/137,172; and 29/137,182 all entitled "Eye Viewing Device" and filed Feb. 14, 2001 and incorporated herein by reference.

An alternative embodiment of the invention is described with reference to FIGS. 3A–3C. In the embodiment shown in FIGS. 3A–3C, light source 14 is disposed directly in the field of view in a highly defocused position in relation to focal planes 26 and 28. By disposing light source 14 on imaging axis 30, light source 14 provides for maximally efficient illumination of a retina 19. Positioning the light source off-axis as is shown by light source 14' results in less-than-maximally efficient retinal illumination, but also reduces glare for reasons that have been discussed herein.

Light source 14 in the embodiment of FIGS. 3A–3C should be positioned in a highly defocused position in relation to any image plane of the eye viewing device conjugate to a patient's retina 19 in an operative position in relation to be positioned in a highly defocused position in relation to any image plane of the eye viewing device conjugate to a patient's retina 19 in an operative position in relation to device 10. As shown in the imaging system diagrams of FIGS. 3A–3C, a highly defocused position for source 14 in relation to an image focal plane conjugate to a retina is provided by disposing source 14 intermediate retinal focal plane 26 and imaging lens 22. In general, source 14 becomes less in focus at any plane conjugate to and including eyepiece focal plane 28 as the source is moved toward imaging lens 22 and away from retinal focal plane 26. Preferably, source 14 is positioned as close as is physically possible to lens 22.

Corneal glare can be reduced in the embodiment of FIGS. 3A–3C if source 14 is disposed in device 10 in a position that is conjugate to the surface of a cornea when the device is in an operative position in relation to a patient. If light source 14 is positioned conjugate to cornea 15, many light rays which do happen to be reflected from cornea 15 are imaged directly onto light source 14. If light source 14 is provided by a reflective element as shown, these light rays correspond to a cornea image and are blocked before reaching eyepiece focal plane 28, thereby reducing corneal glare.

In other specific examples of eye viewing devices designed according to the general configuration described with reference to FIGS. 1A–1E and 3A–3C, the objective lens 16 may be provided by a lens system having a focal length of about 25 mm, and a back focal length of about one-half the focal length. The eye viewing device may be configured so that the lens surface closest to the patient in the objective lens system is positioned about 25 mm from a patient's cornea when in an operative position. The objective lens system accepts parallel or nearly parallel light from a patient's eye and focuses the light to an internal image located at or near the back focal plane 26 of the objective. The objective lens system may have a diameter of about 25 mm. Imaging lens 22, meanwhile, may be provided by a lens system having a focal length of about 25 mm, a back focal length of about 18 mm and a clear aperture of about 20 mm. The imaging lens may project an internal image from the objective focal plane 26 to eyepiece focal plane 28 at a magnification of about 0.6×. Eyepiece focal plane 28 may have an aperture of about 8 mm in diameter, corresponding to the focal plane diameter of a typical 20× eyepiece. The axial length from objective lens 16 to eyepiece focal plane 28 may be about 90 to 10 mm. In the illumination system described with reference to FIG. 3C, condenser lens 20 may be provided by a condenser system having a numerical aperture of about 0.2 to 0.4, working at a magnification of about 1× to 2×, with a focal length of about 9 mm. In the embodiment of FIGS. 1A–1E, aperture stop 32 may be positioned substantially normal to axis 30 and approximately halfway between the most rearward point of light source 14 and the most forward point of imaging lens 22. Aperture stop 32 may have an aperture diameter of about 4.6 mm.

Figure 4:
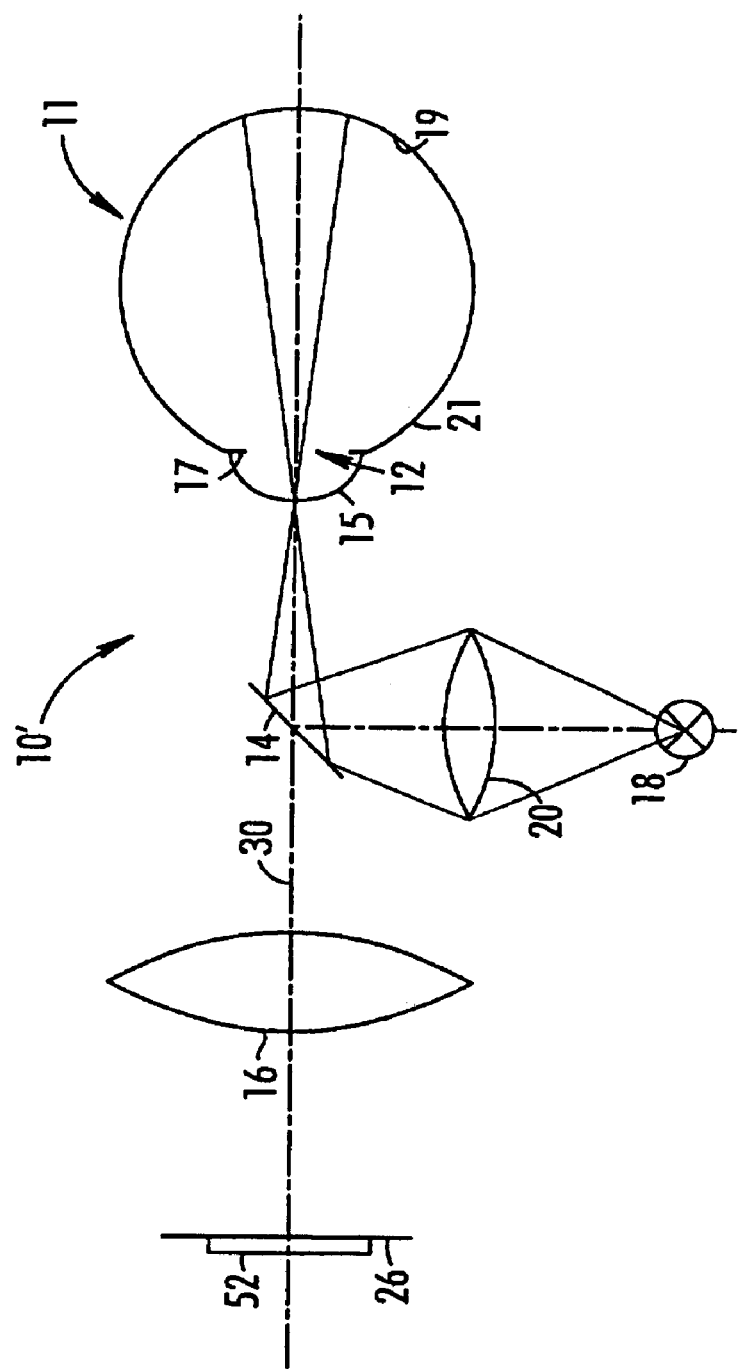
FIG. 4 is a functional schematic diagram of another embodiment of the invention having a defocused light source.

An alternative optical configuration for the eye viewing device of FIGS. 3A–3C having a defocused light source is described with reference to FIG. 4. In the eye viewing device of FIG. 4, light source 14 is disposed forward of objective lens 16 and imaging lens 22 is deleted. Light source 14 is disposed in a highly defocused position in relation to retinal focal plane 26 by disposing light source 14 in proximity with objective lens 16. In the embodiment of FIG. 4, objective lens 16 does not form part of the optical illumination system. Instead, illumination light rays which converge at a cornea 15 and diverge toward a retina 19 are formed by disposing condenser lens 20 in relationship with light source mirror 14 such that light rays reflected from the mirror converge after being reflected. Further with reference to the embodiment of FIG. 4, eyepiece lens 24 may optionally be removed and replaced with image sensor 52, such as a CCD image sensor, which is positioned on retinal focal plane 26. A processor system (not shown) in communication with sensor 52, can be configured to capture image signals generated by sensor 52, process such signals, and if desirable, electronically reverse or magnify any captured images to accomplish the function provided optically by imaging lens 22 of the eye viewing device of FIGS. 1A–3C.

The conventional lenses in the systems described hereinabove can be replaced with similarly functioning optical elements such as diffractive lenses, binary gratings, phase filters, holographic optical elements (HOE), gradient-index lenses, and hybrid optical elements.

Figure 5:
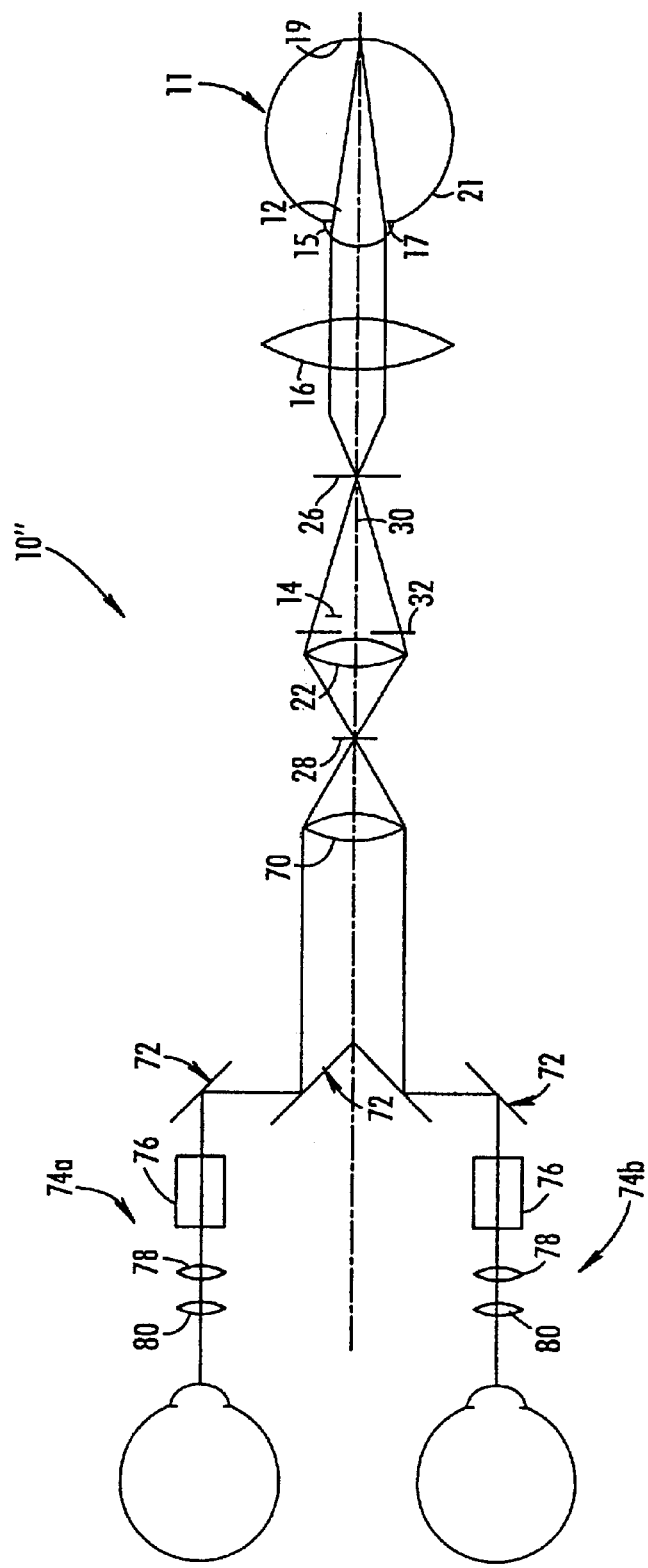
FIG. 5 is functional schematic diagram of the invention configured for binocular viewing.

The invention can be adapted to provide binocular viewing as is illustrated by the embodiments of FIG. 5. As seen in FIG. 5, a binocular eye viewing device according to the invention typically includes a collimating optical element 70 for collimating light rays of the imaging path, and separating optics 72 for splitting light rays transmitted by collimating optics 70 into two separate imaging paths 74A and 74B. Separating optics 72 typically include a combination of such optical elements as prisms and/or mirrors. Continuing with reference to FIG. 5, binocular eye viewing device 10" may further include orientation optics 76 disposed in each binocular imaging path 74A, 74B for setting the orientation of images transmitted by separating optics as is necessary. Orientation optics 76 may include such optical elements as prism and/or mirror optical elements. Binocular eye viewing device 10" may further include decollimation optics 78 and eyepiece optics 80 disposed in each imaging path 74A and 74B. Each eyepiece optics 80 collimates light so that images can be perceived by a viewer. The eye tubes (not shown) of eyepiece optics 80 may be arranged in an orientation slightly diverging toward a viewer's eyes to approximate the direct viewing condition of a target by a pair of eyes.

Several functional aspects of the invention have been described. Certain additional features which may be incorporated in physical embodiments of the invention will now be described in detail.

Figure 6A:
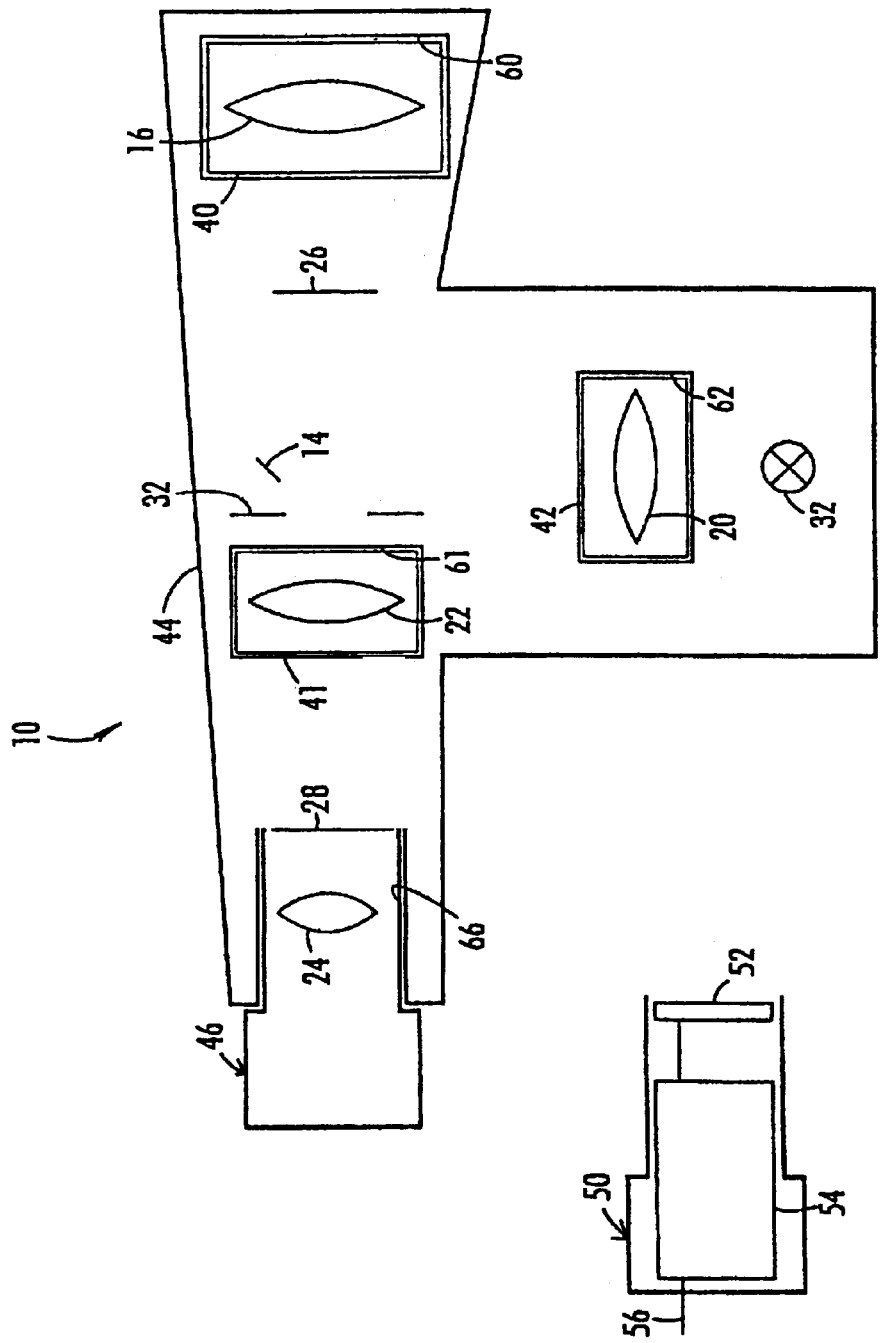
FIGS. 6A–6K are physical schematic diagrams illustrating various features which may be incorporated in certain specific embodiments of the invention.

Shown in FIG. 6A is a physical schematic diagram of an embodiment of the invention which can be reconfigured for optimizing various functional aspects of the eye viewing device. In the embodiment of FIG. 6A, primary housing 44 of eye viewing device 10 includes lens holders 60, 61, 62 and 66 and replaceable lens modules 40, 41, 42 and 46 replaceably received in their respective holders. As will be explained herein below, replacing a certain lens module or a grouping of lens modules changes functional aspects of the eye viewing device enabling the ophthalmoscope to be optimized for a specific intended use. For example, with reference to FIGS. 1A–1E, and 3A–3C, it is seen that the area of retina 19 that is illuminated by the illumination system depends on the diameter and optical power of objective lens 16 and on the magnification selected for the lens at the operative position of the eye viewing device. This area corresponds to the angle α as shown in FIGS. 1A and 3C. The field of view of the imaging system, meanwhile, also depends on the diameter and optical power of objective lens 16 and on the magnification of the lens at the operative position of the eye viewing device.

It is desirable that eye viewing device 10 images a wide field of view. While a wide field of view and illumination angle, α, are highly desirable for an accurate and efficient diagnosis of various problems, a smaller field of view and illumination angle are desirable for ease of use. As the angle of illumination, α, becomes less steep, illumination light rays are more easily directed into an eye through a pupil, so that entry into an eye is easier. This is because as the illumination angle, α, becomes less steep, light rays from source 14 can be directed through pupil 12 over a greater range of cornea-to-lens distances. Accordingly, in view of the above, it would be beneficial to provide an eye viewing device which could be configured either for optimized field of view or optimized ease of use.

In a preferred embodiment, the imaging system of device 10 images a field that contains the area of a retina that is illuminated by the illumination system. Most preferably the area of the retina that is imaged by the imaging system is about 15 percent to 30 percent larger than the area that is illuminated. This feature provides improved orientation of a viewed field and reduces alignment considerations between illumination and viewing.

A possible embodiment of reconfigurable eye viewing device according to the invention is described with reference to the physical schematic diagram of FIG. 6A. This particular physical layout diagram includes first and second lens modules 40 and 41. First lens module 40 includes objective lens 16, while second lens module 41 includes imaging lens 22. While the field of view and illumination angle depend mainly on the sizing, optical power, and magnification selected for objective lens 16, imaging lens 22 will normally be replaced along with lens 16, since the sizing and optical power of lens 16 are coordinated with those of lens 22. The housing 44 and lens modules 40, 41 are complementarily designed so that the modular lens modules can be manually removed and replaced from housing 44 while maintaining a common eyepiece focal plane 28. In a reconfigurable eye viewing device, a first set of lens modules can be provided to configure the eye viewing device for imaging a wide field of view, while a second set of modules can provide a reduced field of view (but with increased magnification), making the instrument easier to maneuver into an operative position. Such a device can be made easier to use simply by replacing the first set of lens modules with the second set of lens modules.

To complement the change in field of view accomplished by changing the first and second lens modules, the illumination condenser system may also be changed in a modular fashion to optimize the illumination characteristics to suit the user's needs. In all condenser systems with a given condenser size, the ability to collect the light from a light generating light source is balanced with the angle at which the light can be transmitted and the magnification at which the image of the light generating light source is projected. The lenses inside the illumination lens module 42 can be selected such that the illumination system matches the illumination numerical aperture of the given objective module 40.

In a further alternate embodiment, the invention can be adapted to capture electronic images representing an imaged retina. One such embodiment is described with reference to FIG. 6A. In FIG. 6A, an eye viewing device 10 is shown that can be reconfigured for electronic image capture. FIG. 6A shows an eye viewing device adapted so that eyepiece module 46 can be replaced with a video module 50. It is seen that eye viewing device 10 normally includes an eyepiece module 46 having an eyepiece lens 24 which collimates imaging light rays so that a retinal image can be viewed by a user. Eyepiece 46 can be replaced with video module 50 which includes certain components that configure the eye viewing device for video capture. In particular, a video module 50 may contain an image sensor 52, such as a CCD or CMOS image sensor, which is in an operative position in relation to the imaging system when the video module is installed in holder 66. The image sensor 52 is in electrical communication with a processor system 54, typically including a microprocessor and associated memory, which may be programmed to control image sensor 52 and to capture and, possibly, to store image data generated by and received from image sensor 52. While processor system 54 is shown as being disposed in video module 50, it is understood that processor system 54 could be disposed external to video module 50. The video module 50 may further be in communication with display screen external to housing 44 and module 50 and/or a processing system external to housing 44 and to module 50 via a combination of communication link components which comprises cable 56 and associated input/output interfaces, for example, so that video image information corresponding to image signals generated by image sensor 52 can be displayed or otherwise output, and possibly archived. The communication link including cable 56 can be replaced with a combination of communication link components which comprises a wireless transmitter-receiver combination. Image information corresponding to image signals generated by image sensor 52 can also be communicated to electronic components external to module 50 and housing 44 with use of a combination of communication link components including transportable memory structure such as a computer disk, a compact disk or a memory stick. An encoder for encoding such a memory structure may be located in a module as described herein or external to a module in housing 44.

Video module 50 can be designed so that image sensor 52 lies on eyepiece focal plane 28 when module 50 is in an operative position in holder 66. It is seen that an eye viewing device of the invention can be configured for video capture by replacing eyepiece module 46 with a video module 50 without adding or replacing additional lenses of the imaging system. Alternative sized image sensors may also be used, with the addition of image resizing lenses. Such a configuration shifts the location of focal plane 28.

Figure 6B:
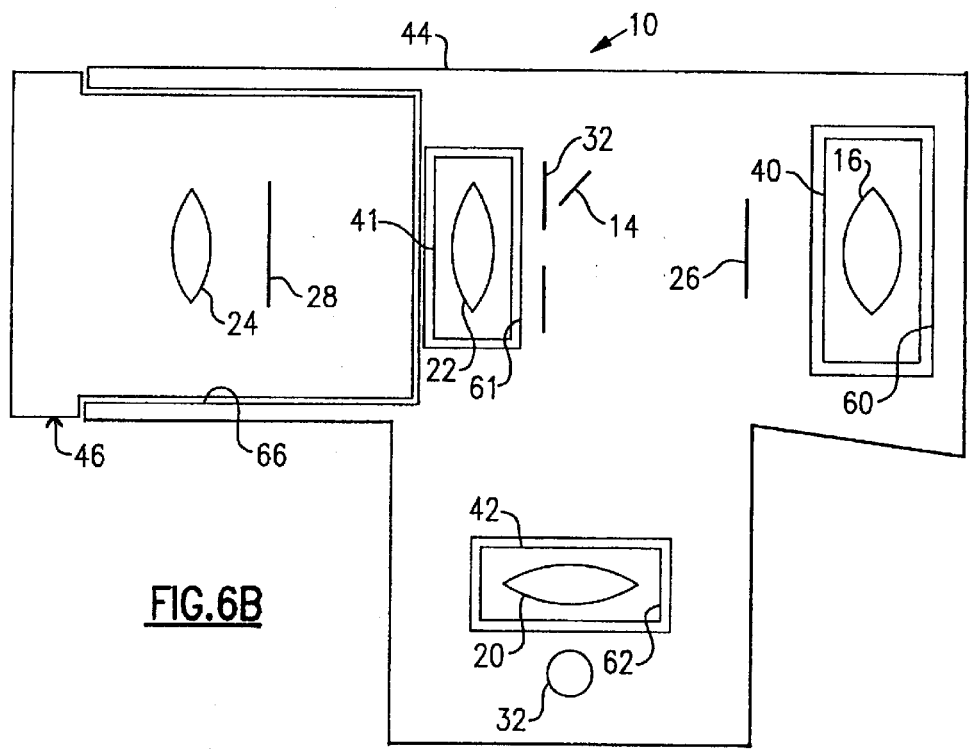
Figure 6C:
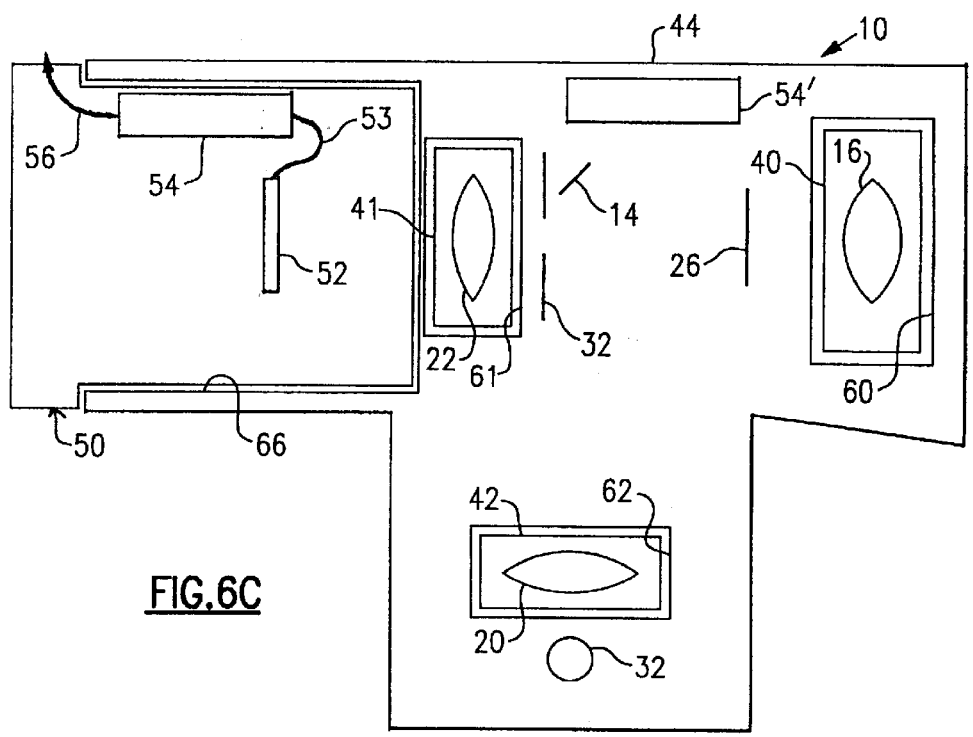

Eye viewing devices having a viewing module holder for receiving various alternative types of viewing modules are shown in FIGS. 6B–6I. Viewing module 46 of FIG. 6B is an alternative version of eyepiece viewing module 46 shown in FIG. 6A. Viewing module 50 of FIG. 6C is an alternative version of video viewing module 50 shown in FIG. 6A.

Figure 6D:
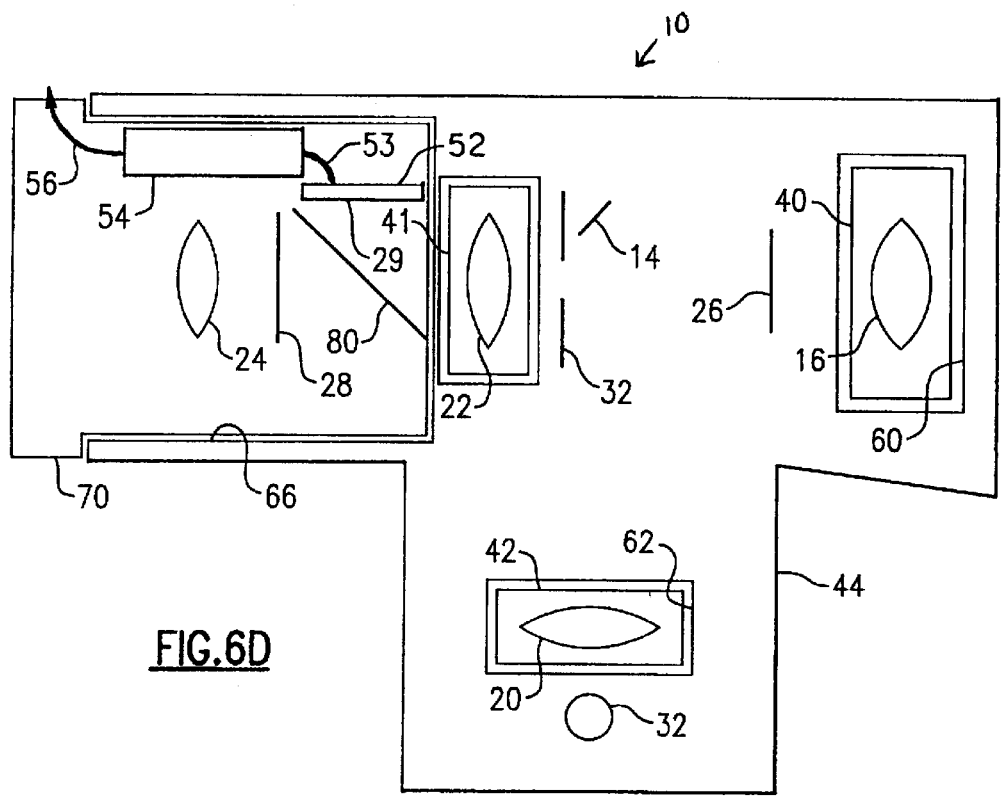

FIG. 6D shows a viewing module 70 adapted to provide both optical viewing and video capture. Viewing module 70 includes a beam splitter 80 for splitting the retinal image and generating a pair of retinal image focal planes, a first, eyepiece focal plane 28, and a second retinal image focal plane 29 at which image sensor 52 is disposed. Viewing module 70, like viewing module 50, includes processor system 54 in communication with image sensor 52 via lead 53 for controlling image sensor 52 and capturing and possibly storing image data corresponding to image signals generated by image sensor 52. Processor system 54 may be programmed to electronically generate a mirror image of the image formed at image sensor 52. Video module 70 further includes lead 56 for providing communication of video images and data with external displays and/or external processing systems.

Shown as being located inside module 70, processor system 54 could in the alternative be positioned at a position external to the module but inside housing 44 as is indicated by processor system 54' of FIG. 6C or at a location external to both module 70 and housing 44. If the processor system associated with any one of the viewing modules described herein having an image sensor 52 is located external to the module but inside housing as is indicated by the embodiment of FIG. 6C, then the processor system 54' and image sensor 52 should be arranged so that an electrical connection is made between the processor system 54' and image sensor 52 when the viewing module having the image sensor is fitted into the viewing module holder 66 of the eye viewing device 10. Such an electrical connection can be provided by positioning complementarily mounted mating connectors in the viewing module and primary device housing 44, respectively, such as mating connectors 85 shown in FIG. 6I.

Mating connectors such as connectors 85 may also serve to facilitate linkage between an electrical component of any one of the viewing modules described and a power supply of a device. For example, mating connectors 85 in the embodiment of FIG. 6I may be adapted so that processor system 54 is electrically linked to a battery supply power source in proximity with light source 32 when connectors of mating connectors 85 are mated together.

Further, it will be understood that the processor system receiving image signals from image sensor 52 in any one of the embodiments described herein need not be located within a viewing module or within housing 44. The processor system receiving image signals from image sensor may be located externally relative to both housing 44, and the viewing module and may be provided, for example, by a processor system of a personal computer. If an eye viewing device according to the invention includes an image information processing processor system located a substantial distance away from an image signals generating image sensor, it is useful to configure the processor system and image sensor so that the image sensor and processor system communicate with one another via a high speed communication technology, such as Universal Serial Bus communication technology.

Figure 6E:
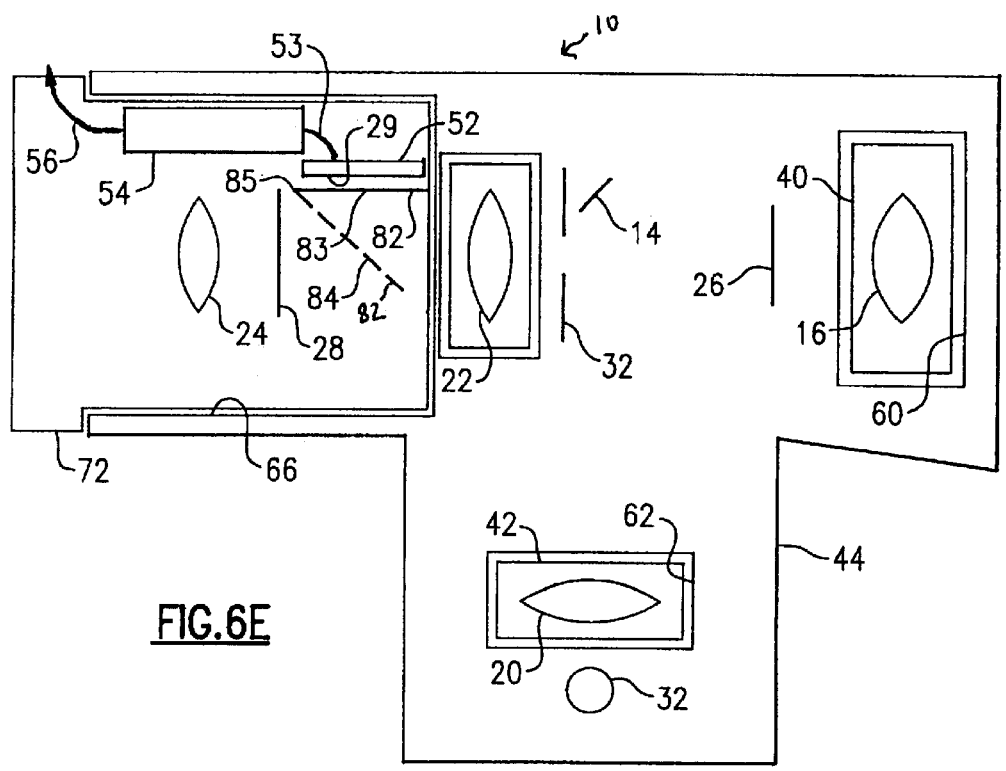

An embodiment of a viewing module similar to the viewing module 70 of FIG. 6D is shown in FIG. 6E. The viewing module of FIG. 6E includes all of the elements of viewing module 70 of FIG. 6D except that viewing module 72 includes a two-position mirror 82 in place of beam splitter 80 FIG. 6D. Two-position mirror 82 is moveable between two positions. In a first position, indicated by solid line 83 mirror is in a position such that a retinal image is formed at eyepiece focal plane 28. In a second position, indicated by dashed line 84, mirror 82 is in a position such that a retinal image is formed at image sensor 52. Mirror 82 may be hingely mounted within viewing module 72 as is indicated by pivot point 85. Mirror 82 may be adapted to be manually moveable between the first and second positions or else mirror 82 may be adapted to be movable by means of motor motion.

Figure 6F:
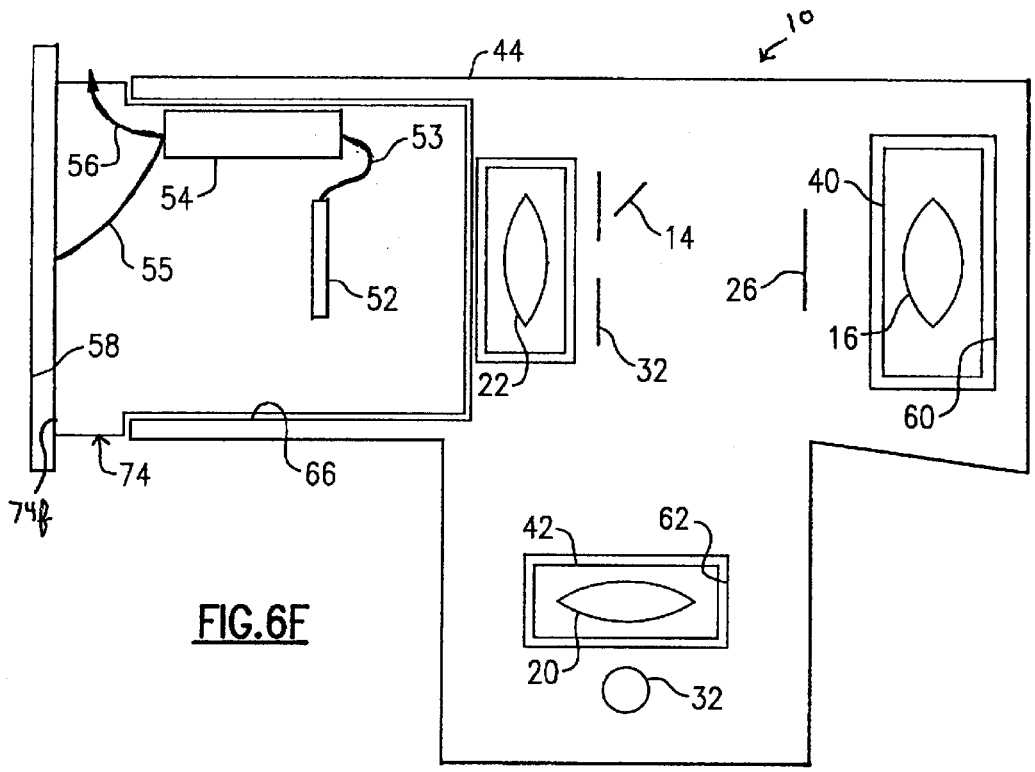

In FIG. 6F, a viewing module received in a viewing module holder 66 is shown that contains a built-in display 58. In viewing module 74, image sensor 52 is positioned at the position of eyepiece focal plane 28 when the module is properly received in holder 66. Image sensor 52 is in communication with processor system 54 programmed to control and capture image data corresponding to image signals generated by image sensor 52. In addition to being in communication with image sensor 52 processor system 54 is in communication via lead 55 with a display 58 which is built directly into module 74. Display 58 may be provided, for example, by a light weight LCD display as is well known. Display 58 is conveniently located at the face portion 74f of viewing module 74 as is indicated by FIG. 6F. Viewing module 74 may include, in addition, a lead 56 for providing external communication of video images and/or other data with an external display or processing system located externally with respect to the viewing module and housing 44.

Figure 6G:
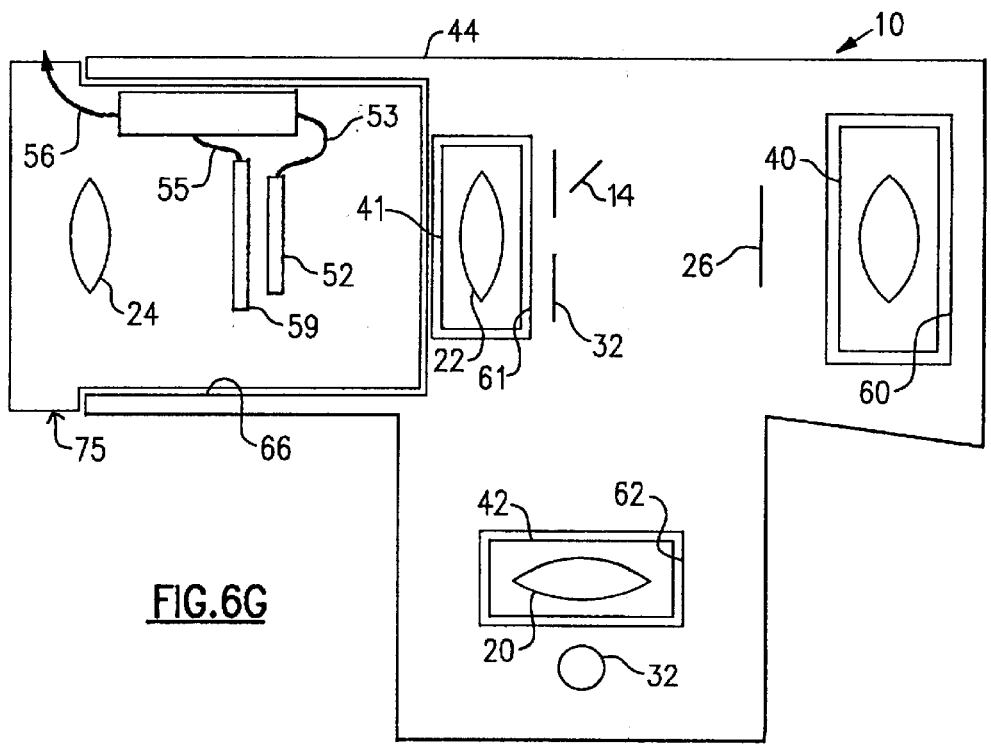

The viewing module 75 of FIG. 6G is similar to the viewing module of FIG. 6F except that externally mounted display 58 is replaced with an interior mounted display 59 mounted at an interior of module 75. Display 59 is preferably a miniature LCD display. Viewing module 75 may include an eyepiece lens 24 for collimating light rays generated by display 59.

Figure 6H:
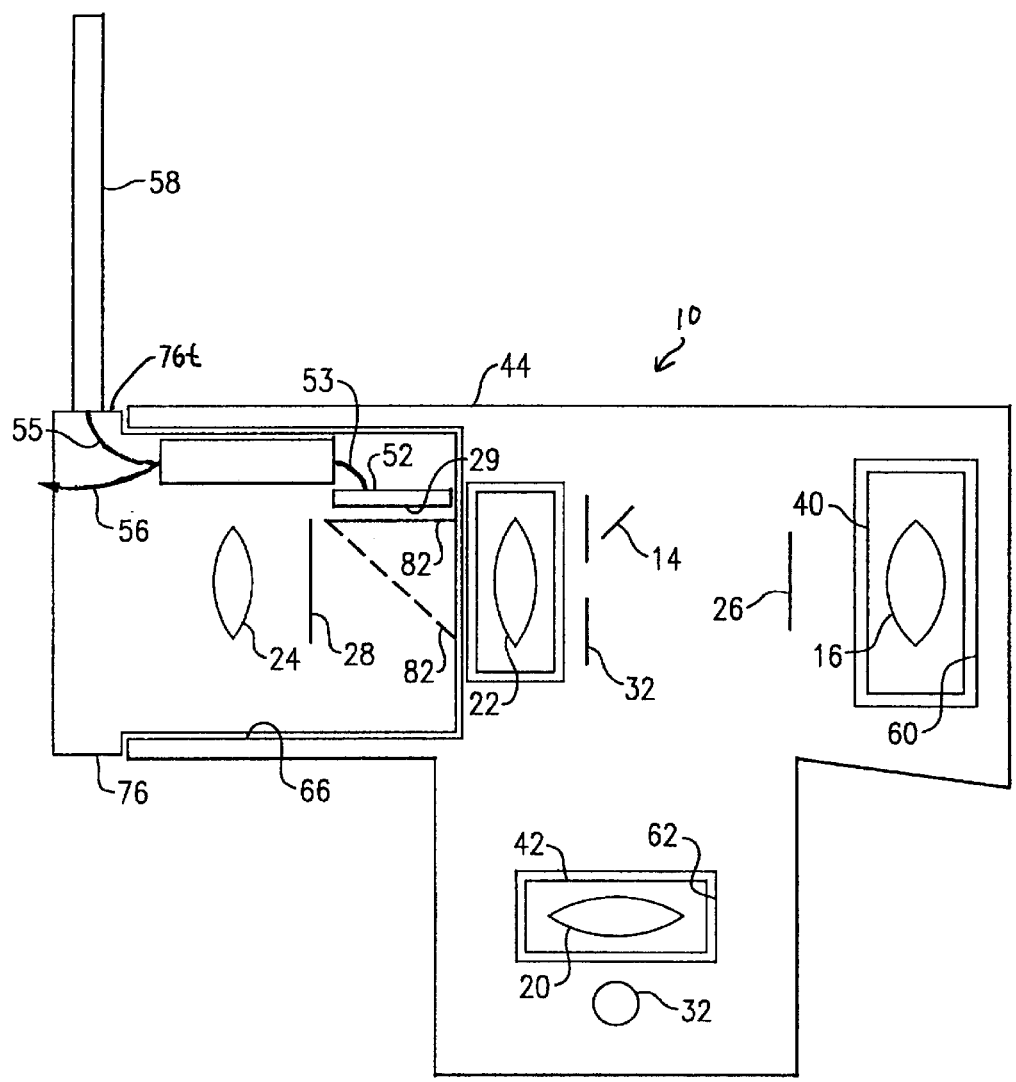
Figure 6I:
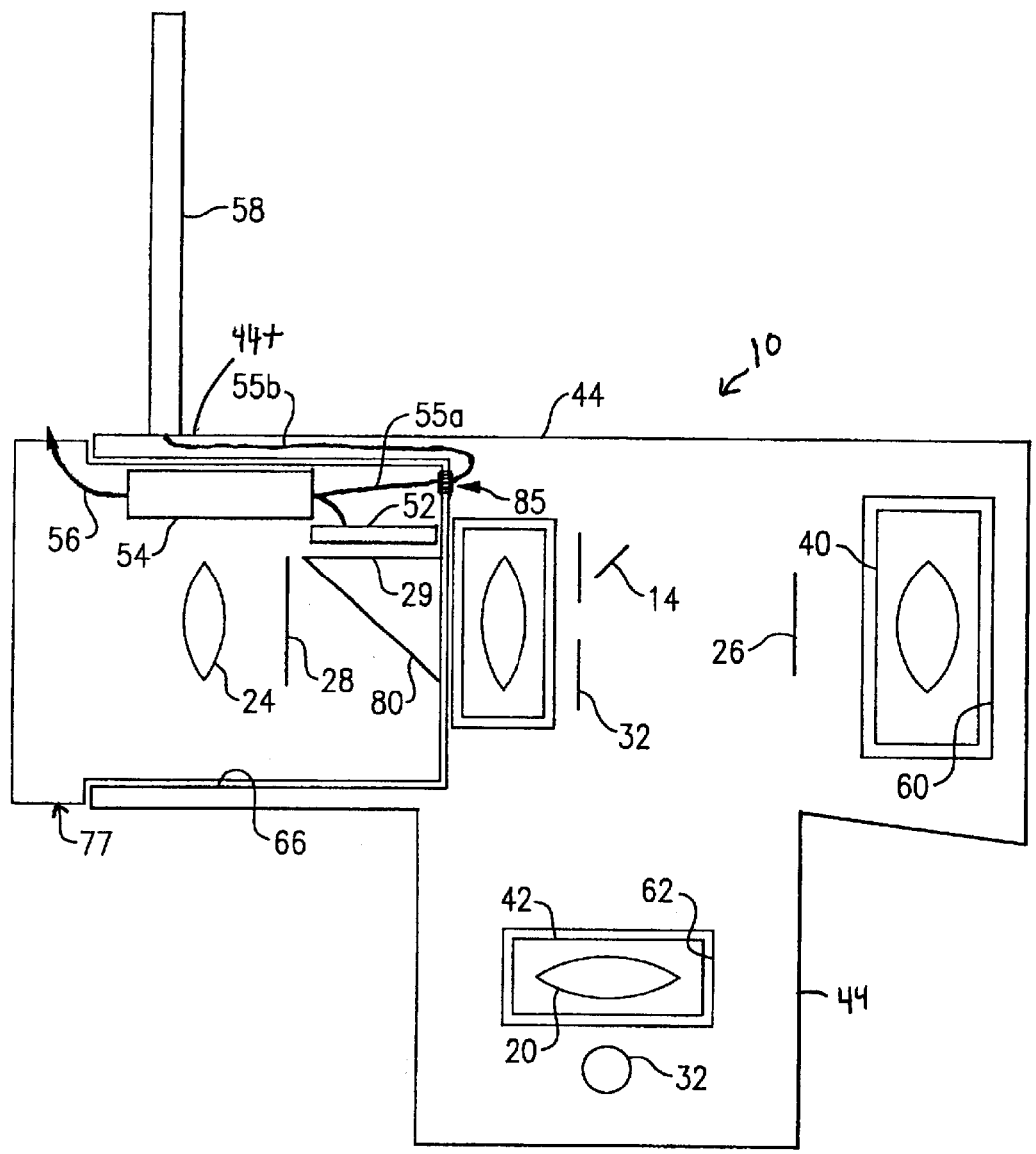

Alternative embodiments of eye viewing devices having built-in or attachable displays are shown in FIGS. 6H and 6I. In the embodiment of FIG. 6H, viewing module 76 includes a display 58 mounted to a top surface 76t of an externally extending portion of module 76. In the embodiment of FIG. 6I, a display 58 is fixedly mounted to a top surface 44t of primary device housing 44. Display 58 could in the alternative be detachably mounted to housing 44 or pivotally attached to housing 44. In the embodiment of FIG. 6I, viewing module 77 includes lead 55A that matingly connects to lead 55B in communication with display 58 when module 77 is received in holder 66. The mating connection between leads 55A and 55B may be provided by complementarily mounted mating connectors 85.

The viewing modules 46, 50, 70, 72, 74, 75, 76 and 77 preferably have similarly sized outer housings so that each may be fitted into a single viewing module holder which is adapted to receive one viewing module at a time. One or more of the above viewing modules may be sold or made available in a system wherein viewing modules can be interchanged for optimization of an eye viewing device for a particular application. A viewing module according to the invention is adapted to be held in place in a complementarily formed holder by friction forces or other known retaining means.

Of course, the elements incorporated in the above-described removably installable viewing modules 46, 50, 70, 72, 74, 75, 76 and 77 can be permanently mounted in an eye viewing device that does not contain a viewing module holder.

Figure 6J:
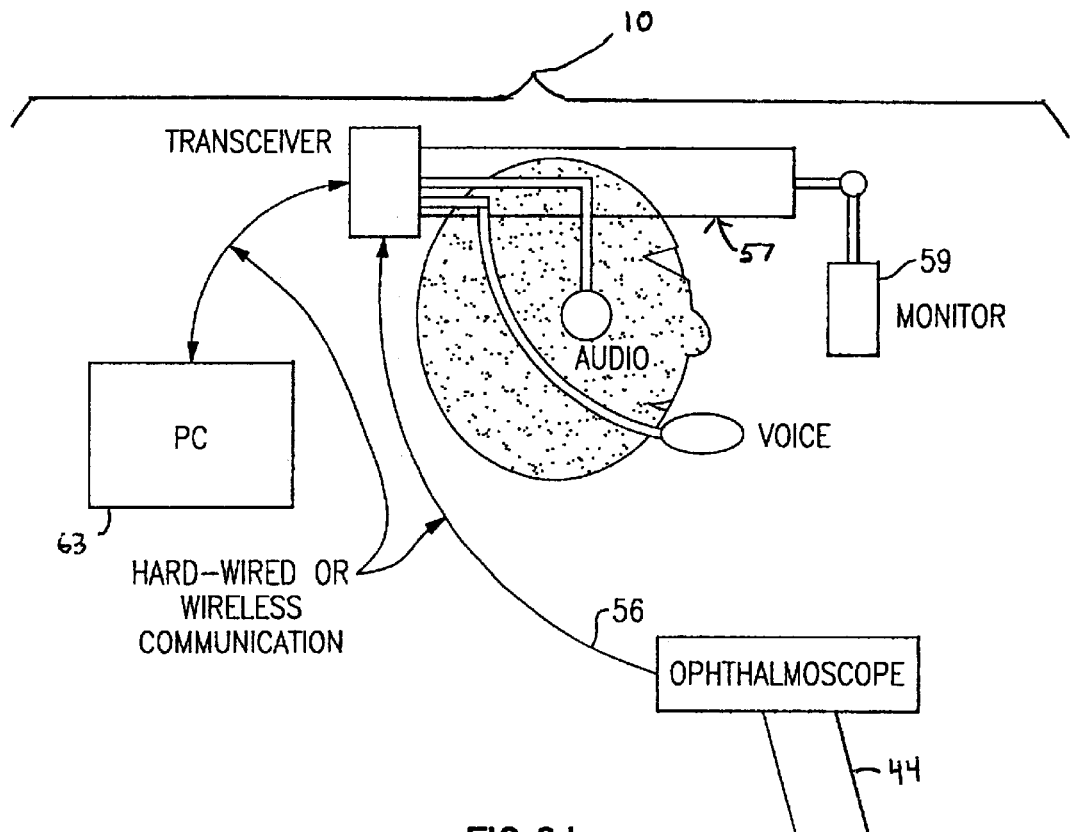
Figure 6K:
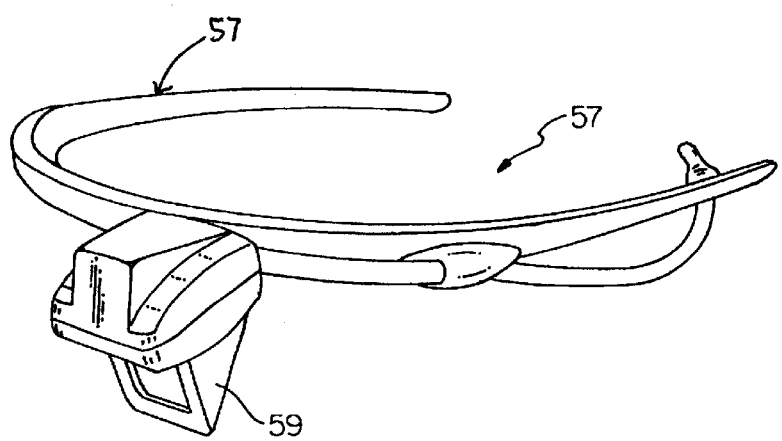

As indicated above, viewing modules having a processor system 54 for processing images may include a lead 56 for providing communication between the processor system and an external display device or processor system external to module and housing 44. One type of external display which may be in electrical communication with viewing module having a video processor system is a head mounted display assembly 57 including a display 59 as shown in FIGS. 6J and 6K. Head mounted displays are useful in enhancing the mobility of a viewer. In the embodiment of FIG. 6J, an eye viewing device 10 includes a head mounted display assembly 57, voice activated control, an audio feedback means, and a personal computer 63. From the embodiment of FIG. 6J it is seen that the elements of an eye viewing device can be spread out over several physically separate components including primary device housing 44, a viewing module, a personal computer 63 and a video assembly 57.

It will be understood that the image sensor referred to in any one of the above viewing modules having an image sensor may be any commercially available image sensor. For example the image sensor may be a visible light image sensor or an image sensor that is selectively responsive to light in a specific band, such as an infrared or ultraviolet image sensor. The image sensor may also be a spectral imaging type image sensor which makes available spectral profile data characterizing the spectrum of light incident at each pixel of the image sensor. In addition, processor system 54 and image sensor 52 can be incorporated in a single piece of silicon. Image sensor 52 and processor system can readily be integrated in a single piece of silicon utilizing CMOS fabrication methods.

Further, it will be understood that any one of the electrically conductive lines described herein, e.g. lines 53, 55, 55a, 55b and 56 could be replaced with a wireless data communication link such as an IR link or an RF link including an RF line utilizing the "Blue Tooth" communication protocol.

While the present invention has been particularly shown and described with reference to the preferred mode as illustrated in the drawings, it will be understood by one skilled in the art that various changes in detail may be effected therein without departing from the spirit and scope of the invention as defined by the claims.

What is claimed:

1. An eye viewing device comprising:
   a portable housing having an observer end and a patient end;
   an illumination system at least partially disposed in said housing;
   an imaging system at least partially disposed in said housing;
   an image sensor generating image signals;
   a processor system processing image information corresponding to image signals generated by said image sensor;
   a module holder defined by said housing at said observer end; and
   a replaceable module comprising at least said image sensor replaceably received in said holder.

2. The eye viewing device of claim 1, wherein said replaceable module further comprises said processor system.

3. The eye viewing device of claim 1, further comprising an electronic display in communication with said processor system.

4. The eye viewing device of claim 1, wherein said replaceable module further comprises a display in communication with said processor system.

5. The eye viewing device of claim 4, wherein said display is externally mounted on said module.

6. The eye viewing device of claim 4, wherein said display is externally mounted on a face of said module.

7. The eye viewing device of claim 4, wherein said display is rigidly mounted on said module.

8. The eye viewing device of claim 4, wherein said display is internally mounted in an interior of said module.

9. The eye viewing device of claim 4, wherein said display is mounted on a top of said housing.

10. The eye viewing device of claim 1, wherein said device includes a head worn display apparatus which includes a display.

11. The eye viewing device of claim 1, wherein said device includes a communication link component facilitating communication of image information externally from said housing.

12. The eye viewing device of claim 11, wherein said replaceable module further comprises said communication link.

13. The eye viewing device of claim 11, wherein said communication link includes a cable.

14. The eye viewing device of claim 11, wherein said communication link comprises a wireless communication link.

15. The eye viewing device of claim 11, wherein said communication link comprises a transportable memory structure.

16. The eye viewing device of claim 2, further comprising an electronic display.

17. The eye viewing device of claim 11, wherein said device further includes an electronic display spaced apart from said housing and said module, and in communication with said communication link.

18. The eye viewing device of claim 1, wherein said housing and said module include complementary mating electrical connectors which are adapted to mate when said module is received in said holder.

19. The eye viewing device of claim 18, wherein said processor system is incorporated in said housing and wherein said mating electrical connectors are adapted to provide breakable communication between said image sensor and said processor system.

20. The eye viewing device of claim 18, wherein said processor system is incorporated in said module, and wherein said device further includes a display mounted on said housing, wherein said mating electrical connectors provide breakable communication between said processor system and said display.

21. The device of claim 3, wherein said device includes a battery power supply incorporated in said housing, wherein said mating connectors proved breakable communication between an electronic component of said module and said power supply.

22. The device of claim 3, wherein said module further comprises a communication link component facilitating communication of image information externally from said housing.

23. An eye viewing device system comprising:
a housing having an observer end and a patient end;
an illumination system at least partially disposed in said housing;
an imaging system at least partially disposed in said housing;
a module holder defined by said housing at said observer end; and
at least first and second replaceable modules, each replaceably receivable in said holder, said holder adapted to receive one of said modules at a given time, wherein said first module comprises an eyepiece lens facilitating direct view of an eye structure and said second module comprises at least an image sensor generating image signals corresponding to an eye structure.

24. The system of claim 23, wherein said second module further comprises an electronic display.

25. The system of claim 23, wherein said second module further comprises a face mounted display.

26. The system of claim 23, wherein said second module further comprises an externally mounted display.

27. The system of claim 23, wherein said second module further comprises an electronic Display mounted in an interior of said module.

28. The system of claim 23, further comprising a communication link component for facilitating communication of image information from said housing.

29. The system of claim 23, wherein said housing is a hand-held housing.

30. The system of claim 23, wherein said holder and said second module comprise complementary mating connectors.

31. The system of claim 23, wherein said illumination system projects a converging cone of light.

32. The system of claim 23, wherein said illumination system and said imaging system include a common objective lens.

33. The system of claim 23, wherein said illumination system projects a converging cone of light converging at an apex, and wherein said imaging system includes an aperture stop disposed to be substantially coaxial with respect to an imaging axis of said imaging system and substantially conjugate said apex.

34. The system of claim 23, wherein said imaging system includes an aperture stop, and wherein said eye viewing device includes an objective lens and an internal light source, wherein a surface of said objective lens closest to said light source is curved substantially concentric about a center of an aperture of said aperture stop, whereby internal glare in said device is reduced.

35. The system of claim 30, wherein said illumination system projects through a pupil, and wherein said imaging system includes an aperture disposed substantially coaxial about an imaging axis of said imaging system and substantially conjugate said pupil, when said illumination system projects substantially a maximum amount of light through said pupil.

36. The eye viewing device of claim 1, wherein said housing is hand held, and wherein said device is configured for viewing a retina.

37. The eye viewing device of claim 1, wherein said housing is hand held, wherein said device is configured for viewing a retina, and wherein said replaceable module further comprises said processor system.

38. The eye viewing device of claim 1, wherein said housing is hand held, wherein, said device is configured for viewing a retina, wherein said replaceable module further comprises said processor system, and wherein said eye viewing device further includes an electronic display in communication with said processor system.

39. The eye viewing device of claim 1, wherein said housing is hand held, wherein said device is configured for viewing a retina, wherein said replaceable module further includes a display in communication with said processor system, and wherein said display is externally mounted on said replaceable module.

40. The eye viewing device of claim 1, wherein said housing is hand held, wherein said device is configured for viewing a retina, wherein said replaceable module further includes a display in communication with said processor system, and wherein said display is externally mounted on a face of said module.

41. The eye viewing device of claim 1, wherein said housing is hand held, wherein said device is configured for viewing a retina, wherein said replaceable module further includes a display in communication with said processor system, and wherein said display is rigidly mounted on said module.

42. The eye viewing device of claim 1, wherein said housing is hand held, wherein said device is configured for viewing a retina, wherein said replaceable module further includes a display in communication with said processor system, and wherein said display is internally mounted in an interior of said module.

43. The eye viewing device of claim 1, wherein said housing is hand held, wherein said device is configured for viewing a retina, wherein said replaceable module further includes a display in communication with said processor system, and wherein said display is mounted on a top of said module.

44. The eye viewing device of claim 1, wherein said illumination system projects a converging cone of light.

45. The eye viewing device of claim 1, wherein said illumination system projects a converging cone of light converging at an apex, and wherein said imaging system includes an aperture stop disposed conjugate to said apex.

46. The eye viewing device of claim 2, wherein said imaging system includes an aperture stop disposed so that said aperture stop is substantially conjugate a pupil of a patient when said device is in an operative position.

47. The eye viewing device of claim 1, wherein said imaging system includes an aperture stop and an objective lens, and wherein said illumination system includes a light source, and wherein a surface of said objective lens closest said light source is curved substantially concentric about an aperture of said aperture stop.

48. A retinal viewing device system comprising:
a hand held housing having an observer end and a patient end;
an illumination system at least partially disposed in said housing;
an imaging system at least partially disposed in said housing;
a module holder defined by said housing at said observer end; and
at least first and second replaceable modules, each replaceably receivable in said holder, said holder adapted to receive one of said modules at a given time, wherein said first module comprises an eyepiece lens facilitating direct view of an eye structure and said second module comprises at least an image sensor for generating image signals corresponding to an eye structure.

49. The system of claim 48, wherein said second module further comprises an electronic display.

50. The system of claim 48, wherein said second module further comprises a face mounted display.

51. The system of claim 48, wherein said second module further comprises an externally mounted display.

52. The system of claim 48, wherein said second module further comprises an electronic display mounted in an interior of said module.

53. The system of claim 48, further comprising a communication link component for facilitating communication of image information from said housing.

54. The system of claim 48, wherein said illumination system includes a light generating light source, where said housing includes a first part extending coextensively with an imaging axis of said imaging system, and a second part extending transverse to said first part, and wherein said light generating light source is disposed in said second part.

55. The system of claim 48, wherein said holder and said second module comprise complementary mating connectors.

56. The system of claim 48, wherein said illumination system projects a converging cone of light.

57. The system of claim 48, wherein said illumination system and said imaging system include a common objective lens.

58. The system of claim 48, wherein said illumination system projects a converging cone of light converging at an apex, and wherein said imaging system includes an aperture stop disposed to be substantially coaxial with respect to an imaging axis of said imaging system and substantially conjugate said apex.

59. The system of claim 48, wherein said imaging system includes an aperture stop, and wherein said eye viewing device includes an objective lens and an internal light source, wherein a surface of said objective lens closest to said light source is curved substantially concentric about a center of an aperture of said aperture stop, whereby internal glare in said is reduced.

60. The system of claim 48, wherein said illumination system projects light through a pupil, and wherein said imaging system includes an aperture disposed substantially coaxial about an imaging axis of said imaging system and substantially conjugate said pupil, when said eye viewing device is in an operative position.

61. A hand held retina viewing device comprising:
a housing:
an image sensor generating image signals;
an imaging system including an imaging axis;
an illumination system projecting a converging cone of light converging at an apex and diverging thereafter; and
a moving mirror disposed in said housing moveable between a first position at which a retinal image focal plane is defined at an active surface of said image sensor and a second position permitting visual viewing of said retina,
wherein said imaging system further includes an aperture stop disposed in said housing substantially conjugate to said apex.

62. The device of claim 61, further including a holder receiving a replaceable module, and wherein said moving mirror is incorporated in a replaceable module replaceably received in said holder.

63. The eye viewing device of claim 61, wherein an aperture stop is sized to substantially correspond to a size of a pupil.

64. The eye viewing device of claim 61, wherein an aperture of said aperture stop is sized substantially according to the formula d=2 m millimeters where d is a diameter of the aperture and m is the magnification of said pupil in a plane of an aperture stop.

65. The eye viewing device of claim 61, wherein said illumination system includes a light source positioned off-axis with respect to said imaging axis, whereby internal and corneal glare in said device is reduced.

66. The eye viewing device of claim 65, wherein said off-axis positioned light source is a light generating light source.

67. The eye viewing device of claim 65, wherein said off-axis positioned light source is provided by a light reflective element.

68. The eye viewing device of claim 61, wherein said imaging system includes an objective lens and said illumination system includes a light source, said objective lens having a first surface closest to said light source curved substantially concentric about a center of an aperture of said aperture stop, whereby internal glare in said device is reduced.

69. The eye viewing device of claim 61, wherein said illumination system includes a light source positioned outside of a border between received and blocked light defined by said aperture stop, whereby said light source has no obscuring effect on images received by said viewing device.

70. The eye viewing device of claim 61, wherein said illumination system includes a light source positioned outside of a border between received and blocked light defined by said aperture stop and wherein said imaging system includes an objective lens having a curved first surface curved concentric about a center of an aperture of said aperture stop, whereby said light source has no obscuring effect on images received by said viewing device, and whereby incident light reflected from said first surface is blocked by said aperture stop.

71. The eye viewing device of claim 61, wherein said device is devoid of a beam splitter.

72. The eye viewing device of claim 61, wherein a retinal field of view of said imaging system is larger than a retinal area of illumination of said illumination system.

73. The eye viewing device of claim 61, wherein a retinal field of view of said imaging system is between about 15 to 30 percent larger than a retinal area of illumination of said illumination system.

74. The eye viewing device of claim 61, wherein said aperture stop is disposed in said device so that said aperture stop is substantially conjugate to said pupil when said illumination system projects substantially a maximum amount of light through said pupil.

75. The eye viewing device of claim 61, wherein said imaging system includes an objective lens disposed in a path of illumination light rays generated by said illumination system.

76. The eye viewing device of claim 61, wherein said illumination system includes an objective lens disposed so that said imaging axis intersects said objective lens.

77. A hand held retina viewing device comprising:
a housing;
an image sensor generating image signals;
an imaging system including an imaging axis;
an illumination system projecting a converging cone of light converging at an apex and diverging thereafter;
wherein said imaging system further includes an aperture stop disposed in said housing substantially conjugate to said apex; and
wherein said retina viewing device is configured to facilitate both visual viewing of said retina and electronic image capturing of an image representing said retina.

78. The retina viewing device of claim 77, further including a holder receiving a replaceable module, and wherein said device includes a beam splitter incorporated in said replaceable module.

79. The retina viewing device of claim 77, said illumination system includes a mirror, a light generating light source, and a condenser lens converging light from said light generating light source to a point on said mirror.

80. The retina viewing device of claim an aperture of said aperture stop is sized substantially according to the formula d=2 m millimeters where d is a diameter of the aperture and m is the magnification of a pupil in a plane of said aperture stop when said device is in an operative position.

81. The retina viewing device of claim 77, wherein said imaging system includes an objective lens and said illumination system includes a light source, said objective lens having a curved first surface closest to said light source curved substantially concentric about a center of an aperture of said aperture stop, whereby internal glare in paid device is reduced.

82. The retina viewing device of claim 77, wherein said illumination system includes a light source positioned outside of a border between received and blocked light defined by said aperture stop and wherein said imaging system includes an objective lens having a curved first surface closest to said light source curved concentric about a center of an aperture of said aperture stop, whereby said light source has no obscuring effect on images received by said retina viewing device, and whereby incident light reflected from said first surface is blocked by said aperture stop.

83. The retina viewing device of claim 77, wherein said retina viewing device further includes a holder and first and second replaceable modules, wherein said holder is adapted to receive one of said modules at a given time, wherein said first module comprises an eyepiece lens facilitating direct view of said retina and said second module comprises at least an image sensor for generating image signals corresponding to said retina.

84. The retina viewing device of claim 77, wherein said eye viewing device includes an image sensor generating image signals and a moving mirror disposed in said housing moveable between a first position at which a retinal image focal plane is defined at an active surface of said image sensor and a second position permitting visual viewing of said retina.

85. The retina viewing device of claim 84, further including holder, and a replaceable module replaceably received in said holder, wherein said moving mirror is disposed in said module.

86. The retina viewing device of claim 77, wherein said retina viewing device includes an image sensor generating image signals and a beam splitter generating a first retinal image focal plane to facilitate direct viewing of said retina and a second retinal image focal plane, said second retinal image focal plane being generated at said image sensor.

87. The retina viewing device of claim 86, further including holder, and a replaceable module replaceably received in said holder, wherein said beam splitter is disposed in said module.

88. A hand held retina viewing device for viewing a retina of an eye having a pupil, said hand held retina viewing device comprising:
an illumination system for illuminating said retina;
an imaging system having an imaging axis, wherein said illumination system and said imaging system include, a common objective lens;
an aperture stop disposed in said device substantially coaxial with said imaging axis, wherein an operative position of said device is achieved when said aperture stop is positioned substantially conjugate to said pupil, and wherein said illumination system includes a light source positioned off-axis with respect to said imaging axis so that internal and corneal glare in said device is reduced; and
wherein said eye viewing device is configured to facilitate both visual viewing of said retina and electronic image capturing of an image representing said retina.

89. The retina viewing device of claim 88, wherein an aperture of said aperture stop is sized to substantially correspond to a size of said pupil.

90. The retina viewing device of claim 88, wherein said light source is provided by a light reflecting mirror.

91. The retina viewing device of claim 88, wherein said imaging system includes an objective lens, said objective lens having a first surface closest to said light source curved substantially concentric about a center of an aperture of said aperture stop, whereby internal glare in said device is reduced.

92. The retina viewing device of claim 88, wherein said off-axis positioned light source is positioned outside of an aperture of said aperture stop, whereby said light source has no obscuring effect on images received by said viewing device.

93. The retina viewing device of claim 88, wherein said off-axis positioned light source is positioned outside of a border between received and blocked light defined by said aperture stop and wherein said imaging system includes an objective lens having a curved first surface curved concentric about a center of said aperture stop, whereby said light source has no obscuring effect on images received by said viewing device, and whereby incident light reflected from said first surface is blocked by said aperture stop.

94. The retina viewing device of claim 88, wherein a retinal field of view of said imaging system is larger than a retinal area of illumination of said illumination system.

95. The retina viewing device of claim 88, wherein a retinal field of view of said imaging system is between about 15 to 30 percent larger than a retinal area of illumination of said illumination system.

96. The retina viewing device of claim 88, wherein said retina viewing device further includes a holder and first and second replaceable modules, wherein said holder is adapted to receive one of said modules at a given time, wherein said first module comprises an eyepiece lens facilitating direct view of said retina and said second module comprises at least an image sensor for generating image signals corresponding to said retina.

97. The retina viewing device of claim 88, wherein said eye viewing device includes an image sensor generating image signals and a moving mirror disposed in said housing moveable between a first position at which a retinal image focal plane is defined at an active surface of said image sensor and a second position permitting visual viewing of said retina.

98. The retina viewing device of claim 97, further including holder, and a replaceable module replaceably received in said holder, wherein said moving mirror is disposed in said module.

99. The retina viewing device of claim 88, wherein said retina viewing device includes an image sensor generating image signals and a beam splitter generating a first retinal image focal plane to facilitate direct viewing of said retina and a second retinal image focal plane, said second retinal image focal plane being generated at said image sensor.

100. The retina viewing device of claim 99, further including holder, and a replaceable module replaceably received in said holder, wherein said beam splitter is disposed in said module.

* * * * *